(12) United States Patent
Qian et al.

(10) Patent No.: US 7,307,177 B2
(45) Date of Patent: Dec. 11, 2007

(54) METALLOCENE COMPLEXES, THEIR SYNTHESIS AND USE IN CATALYST SYSTEMS FOR OLEFIN POLYMERIZATION

(75) Inventors: Yanlong Qian, deceased, late of Shanghai (CN); by Jiling Huang, legal representative, Shanghai (CN); Jo Ann M. Canich, Houston, TX (US); Catalina L. Coker, Baytown, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 87 days.

(21) Appl. No.: 11/284,885

(22) Filed: Nov. 22, 2005

(65) Prior Publication Data

US 2006/0135353 A1  Jun. 22, 2006

Related U.S. Application Data

(60) Provisional application No. 60/637,336, filed on Dec. 17, 2004.

(51) Int. Cl.
*C07F 17/00* (2006.01)
*C08F 4/6392* (2006.01)

(52) U.S. Cl. ............ 556/11; 556/12; 556/53; 502/103; 502/152; 526/131; 526/160; 526/165

(58) Field of Classification Search ........... 556/11, 556/53, 12; 502/103, 152; 526/131, 160, 526/165

See application file for complete search history.

(56) References Cited

U.S. PATENT DOCUMENTS 6,087,290 A   7/2000  Fottinger et al. ............ 502/103
6,630,549 B1  10/2003 Koike ......................... 526/160

OTHER PUBLICATIONS

Walker et al., "Synthesis, Structures, and Ring-Opening Polymerization Reactions on Substituted Cyclopentadienyl Complexes of Zinc", Organometallics, 2003, 22, pp. 797-803.
Yu et al., "Role of Amine Structure and Site Isolation on the Performance of Aminosilica-Immobilized Zirconium CGC-Inspired Ethylene Polymerization Catalysts", Organometallics, 2004, 23, pp. 4089-4096.
Zemanek et al., "Synthesis of {1,3-bis($\eta^5$-tetramethylcyclopentadienyl)-1,1,3,3-tetramethyldisiloxane} dichlorotitanium(IV) via hydrolysis of bis { $\eta^5$-(N,N-dimethylaminodimethylsilyl) tetramethylcyclopentadienyl}dichlorotitanium(IV)", Inorg. Chem. Comm. 4 (2001), pp. 520-525.
Pinkas et al., "Synthesis and structure of bis{$\eta^5$-1,2,3,4-tetramethyl-5-(dimethylsilylsulfido-$\kappa$S)cyclopentadienyl} titanium(IV)", Inorg. Chem. Comm. 7 (2004), pp. 1135-1138.
Ciruelo et al., "Synthesis and reactivity of new silyl substituted monocyclopentadienyl zirconium complexes. X-ray molecular structure of [Zr{$\eta^5$-C$_5$H$_4$(SiMe$_2$CH$_2$Ph)}(CH$_2$Ph)$_3$]", Journal of Organo. Chem. 547 (1997), pp. 287-296.
Gomez et al., "Reactivity of chlorodimethylsilyl-$\eta^5$-cyclopentadienyltrichlorotitanium with nitrogen based donors. X-ray molecular structure of [Ti{ $\eta^5$-C$_5$H$_4$SiMe$_2$[$\eta^1$-N(2,6-Me$_2$C$_6$H$_3$)]}Cl$_2$]" Journal of Organo. Chem. 564 (1998), pp. 93-100.
Alt et al., "Synthesis, characterization and polymerization potential of ansa-metallocene dichloride complexes of titanium, zirconium and hafnium containing of Si—N—Si bridging unit", Journal of Organo. Chem. 564 (1998), pp. 109-114.

(Continued)

*Primary Examiner*—Caixia Lu
(74) *Attorney, Agent, or Firm*—Catherine L. Bell

(57) ABSTRACT

A metallocene complex is represented by the the formula $$(C_pR_5)_nMX_k$$

where $C_p$ (each occurrence) is a cyclopentadienyl group; each of the five R substituents on the or each cyclopentadienyl group is independently selected from hydrogen, $C_1$ to $C_{30}$ substituted or unsubstituted hydrocarbyl, halohydrocarbyl, silylhydrocarbyl or silylhalohydrocarbyl, wherein two adjacent R substituents may be joined to form part of a saturated, partially unsaturated or aromatic monocyclic or polycyclic ring structure, and $SiR'_2NR''_2$ where each of the two R' substituents is independently selected from hydrogen, $C_1$ to $C_{30}$ substituted or unsubstituted hydrocarbyl, halohydrocarbyl, silylhydrocarbyl or silylhalohydrocarbyl, wherein two adjacent R' substituents may be joined to form part of a saturated, partially unsaturated or aromatic monocyclic or polycyclic ring structure, and each of the two R" substituents is independently selected from $C_2$ to $C_{30}$ substituted or unsubstituted hydrocarbyl, halohydrocarbyl, silylhydrocarbyl or silylhalohydrocarbyl, wherein two adjacent R" substituents may be joined to form part of a saturated, partially unsaturated or aromatic monocyclic or polycyclic ring structure; n is 1 or 2; M is a metal of valence m from Groups 4 to 11 of the Periodic Table of Elements, k is equal to m minus n and the or each X substituent is a univalent anionic ligand, or two X substituents are joined and bound to the metal atom to form a metallocycle ring, or two X substituents are joined to form a chelating ligand, a diene ligand, or an alkylidene ligand, provided that at least one R substituent on the or one cyclopentadienyl group is $SiR'_2NR''_2$, provided that at least one R substituent on at least one $C_p$ is $SiR'_2NR''_2$ and provided that one or the $C_p$ may be bridged by a bridging group to another $C_p$ group, or a heteroatom containing group, where the bridging group replaces one R group on the $C_p$ group(s) or a hydrogen on a heteroatom containing group.

22 Claims, No Drawings

OTHER PUBLICATIONS

Ciruelos et al., "Synthetic and reactivity studies of mono- and dicyclopentadienyl titanium, zirconium and hafnium complexes with the chlorodimethylsilyl-cyclopentadienyl ligand. X-ray molecular structure of Hf{($\eta^5$-$C_5H_4$)$SiMe_2OSiMe_2$($\eta^5$-$C_5H_4$)}$Cl_2$ and Zr($\eta^5$-1,3-$^tBu_2C_5H_3$)($\eta^5$-$C_5H_4SiMe_2$-$\eta$-$N^tBu$)Cl", Journal of Organo. Chem., 604 (2000), pp. 103-115.

Pinho et al., "Ground State Modulation in Nickel(III) Chemistry by Controlling Axial Ligation in Complexes with $N_3O_2$ Pentadentate Ligands", Eur. J. Inorg. Chem. 2001, pp. 1483-1493.

Rau et al., "Synthesis, Structure and Reactivity of a Zirconocene Dichloride with ($Me_3Si)_2NSiMe_2$ Side-Chains", Eur. J. Inorg. Chem. 2001, pp. 1785-1788.

Bourke et al., "Ring-Opening Protonolysis of Sila[1]ferrocenophanes as a Route to Stabilized Silylium Ions", Chem. Eur. J. 2005, 11, pp. 1989-2000.

Anon, "Novel Preparation of Transition Metal Dichloride Complexes", Research Disclosure, 2001, 445 (May), P814, No. RD445105.

METALLOCENE COMPLEXES, THEIR SYNTHESIS AND USE IN CATALYST SYSTEMS FOR OLEFIN POLYMERIZATION

CROSS REFERENCE TO RELATED APPLICATION

This application claims the benefit of priority to U.S. Provisional Patent Application No. 60/637,336, filed Dec. 17, 2004 the disclosure of which is incorporated by reference.

FIELD

This invention relates to novel metallocene complexes, a method of their synthesis and their use in catalyst systems for olefin polymerization.

BACKGROUND

Since the discovery of ferrocene in 1951, a large number of metallocenes have been prepared by the combination of compounds prepared from cyclopentadienyl-type, indenyl-type, and fluorenyl-type compounds and various transition metals. Many of such metallocenes have been found useful in catalyst systems for the polymerization of olefins.

It has been noted that variations in the chemical structure of the metallocene can have significant effects upon the suitability of the metallocene as a polymerization catalyst. For example, the type, size and location of substituents on cyclopentadiene ligands have been found to affect the activity of the catalyst, the stereoselectivity of the catalyst, the stability of the catalyst, or various properties of the resulting polymer. However, the effects of various substituents is still largely an empirical matter; that is, experiments must be conducted in order to determine just what effect a particular variation in the chemical structure of the metallocene will have upon its behavior as a polymerization catalyst.

Among the cyclopentadienyl substituents that have been investigated are aminosilyl moieties, at least partly because of the potential for hydrolytic cleavage of the Si—N bond. Thus, for example, the paper entitled Synthesis of {1,3-bis ($\eta^5$-tetramethylcyclopentadienyl)-1,1,3,3-tetramethyldisiloxane}dichlorotitanium (IV) via hydrolysis of bis {$\eta^5$—(N,N-dimethylaminodimethylsilyl)tetramethylcyclopentadienyl} dichlorotitanium (IV) by Zemanek et al. in *Inorganic Chemistry Communications* 2001, 4(9), 520 discloses that bis {(N,N-dimethylaminodimethylsilyl) tetramethylcyclopentadienyl} titanium dichloride undergoes hydrolytic cleavage to produce $TiCl_2(C_5Me_4SiMe_2)_2O$. In addition, the paper entitled Synthesis, Structure and Reactivity of Zirconocene Dichloride with $(Me_3Si)_2$ $NSiMe_2$ Side Chains, by Rau et al. in *European Journal of Inorganic Chemistry* 2001, 1785 discloses the synthesis of the zirconocene $[C_5H_4SiMe_2N(SiMe_3)_2]ZrCl_2$.

U.S. Pat. No. 6,087,290 discloses a Si—N—Si bridged metallocene complex of the formula $[L-SiMe_2NRSiMe_2L]$ $MX_2$ wherein L is a $C_5H_4$, $C_9H_6$ or $C_{13}H_8$ radical; R is an alkyl radical selected from methyl, propyl, butyl, octyl, prop-2-enyl, 2-methoxyethanyl, 3-phenylethyl, 3-phenylpropanyl, and 4-phenylbutanyl.; M is selected from titanium, hafnium, and zirconium; and X is selected from chlorine, bromine, iodine, methyl and diethyl amine. The metallocene complex is produced by contacting a bidentate ligand precursor of the formula $L-SiMe_2-NHR$ with an equimolar amount of an organolithium compound of the formula RLi to form a single deprotonated ligand precursor of the formula $Li[L-SiMe_2-NHR]$, contacting the single deprotonized ligand precursor with half an equivalent of $MX_4$ to produce a precursor complex of the formula $(LSiMe_2NHR)_2MX_2$ and then contacting the precursor complex with another equivalent of $MX_4$.

U.S. Pat. No. 6,630,549 discloses a a method of producing an olefin polymer by continuous slurry polymerization or continuous gaseous phase polymerization in the presence of a metallocene catalyst, exemplified by a compound of the formula:

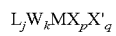

wherein L (each occurrence) independently represents an $\eta$-bonded, cyclic anionic ligand selected from the group consisting of a cyclopentadienyl group, an indenyl group, a tetrahydroindenyl group, a fluorenyl group, a tetrahydrofluorenyl group and an octahydrofluorenyl group, wherein the bonded, cyclic anionic ligand optionally has 1 to 8 substituents, each of which independently has up to 20 non-hydrogen atoms and is independently selected from the group consisting of a $C_1$-$C_{20}$ hydrocarbon group, a halogen, a $C_1$-$C_{12}$ halogen-substituted hydrocarbon group, a $C_1$-$C_{12}$ aminohydrocarbyl group, a $C_1$-$C_{12}$ hydrocarbyloxy group, a $C_1$-$C_{12}$ dihydrocarbylamino group, a $C_1$-$C_{12}$ hydrocarbylphosphino group, a silyl group, an aminosilyl group, a $C_1$-$C_{12}$ hydrocarbyloxysilyl group and a halosilyl group; M represents a transition metal selected from transition metals of Group 4 of the Periodic Table, each independently having a formal oxidation state of +2, +3 or +4, the transition metal being bonded, in a $\eta^5$-bonding mode, to at least one L; W represents a divalent substituent having up to 50 non-hydrogen atoms, which has one valence bonded to L and one valence bonded to M, so that W, L and M together form a metallocycle; X (each occurrence) independently represents a ligand having up to 60 non-hydrogen atoms, which is a monovalent σ-bonded anionic ligand having both valences bonded to M, or a divalent σ-bonded anionic ligand having one valence bonded to M and one valence bonded to L; X' (each occurrence) independently represents a neutral Lewis base ligating compound having up to 40 non-hydrocarbon atoms; j is 1 or 2, with the proviso that, when j is 2, two L ligands are optionally bonded together through a divalent group having up to 20 non-hydrogen atoms, which is selected from the group consisting of a $C_1$-$C_{20}$ hydrocarbadiyl group, a $C_1$-$C_{12}$ halohydrocarbadiyl group, a $C_1$-$C_{12}$ hydrocarbyleneoxy group, a $C_1$-$C_{12}$ hydrocarbyleneamino group, a siladiyl group, a halosiladiyl group and an aminosilane; k is 0 or 1; p is 0, 1 or 2, with the proviso that when X is a monovalent σ-bonded anionic ligand or a divalent σ-bonded anionic ligand having one valence bonded to M and one valence bonded to L, p is an integer which is one or more smaller than the formal oxidation state of M, and that, when X is a divalent σ-bonded anionic ligand having both valences bonded to M, p is an integer which is (j+1) or more smaller than the formal oxidation state of M; and q is 0, 1 or 2.

SUMMARY

This invention relates to a metallocene complex represented by the formula:

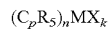

where $C_p$ (each occurrence) is a cyclopentadienyl group; each of the five R substituents on the or each cyclopentadienyl group is independently selected from hydrogen, $C_1$ to $C_{30}$ substituted or unsubstituted hydrocarbyl, halohydrocarbyl, silylhydrocarbyl or silylhalohydrocarbyl, wherein two adjacent R substituents may be joined to form part of a saturated, partially unsaturated or aromatic monocyclic or polycyclic ring structure, and $SiR'_2NR''_2$ where each of the two R' substituents is independently selected from $C_1$ to $C_{30}$ substituted or unsubstituted hydrocarbyl, halohydrocarbyl, silylhydrocarbyl or silylhalohydrocarbyl, and wherein two adjacent R' substituents may be joined to form part of a monocyclic or polycyclic ring structure and each of the two R'' substituents is independently selected from $C_2$ to $C_{30}$ substituted or unsubstituted hydrocarbyl, halohydrocarbyl, silylhydrocarbyl or silylhalohydrocarbyl, wherein two adjacent R'' substituents may be joined to form part of a saturated, partially unsaturated or aromatic monocyclic or polycyclic ring structure, and where a R' and a R'' may join together to form part of a monocyclic or polycyclic ring structure; n is 1 or 2; M is a transition metal of valence m from Groups 4 to 11 of the Periodic Table of Elements, k is equal to m minus n; and the or each X substituent is a univalent anionic ligand, or two X substituents are joined and bound to the metal atom to form a metallocycle ring, or two X substituents are joined to form a chelating ligand, a diene ligand, or an alkylidene ligand, provided that at least one R substituent on at least one Cp is $SiR'2NR''2$ and provided that one or the Cp group may be bridged by a bridging group to another Cp group, or a heteroatom containing group, where the bridging group replaces one R group on the Cp group(s) or a hydrogen on a heteroatom containing group.

In one embodiment, said complex includes a single $SiR'_2NR''_2$ substituent and the remaining R substituents are hydrogen or methyl.

In another embodiment, n is 2 and one R substituent on each cyclopentadienyl group is $SiR'_2NR''_2$ and the remaining R substituents on each cyclopentadienyl group are hydrogen or methyl.

In another embodiment, each R' substituent is $C_1$ to $C_{12}$ hydrocarbyl, such as methyl.

In another embodiment, each R'' substituent is $C_2$ to $C_{12}$ hydrocarbyl, such as iso-propyl.

Alternatively, the R'' substituents of each $SiR'_2NR''_2$ group are joined such that the $NR''_2$ moiety forms a five or six membered nitrogen-containing ring, such as a pyrrolidinyl or piperidinyl ring.

In another embodiment, M is titanium, zirconium or hafnium, and preferably is zirconium or hafnium.

In a further aspect, the invention resides in an olefin polymerization catalyst system comprising a metallocene complex according to said one aspect of the invention and a co-catalyst or activator.

In yet a further aspect, the invention resides in a process for polymerizing at least one olefin monomer in the presence of a catalyst system according to said further aspect of the invention.

DETAILED DESCRIPTION

For the purposes of this invention and the claims thereto when a polymer is referred to as comprising a monomer, the monomer present in the polymer is the polymerized form of the monomer. Likewise when catalyst components are described as comprising neutral stable forms of the components, it is well understood by one of ordinary skill in the art, that the active form of the component is the form that reacts with the monomers to produce polymers. In addition, a reactor is any container(s) in which a chemical reaction occurs.

For the purposes of this invention and the claims thereto the new numbering scheme for the Periodic Table Groups is used as described in CHEMICAL AND ENGINEERING NEWS, 63(5), 27 (1985).

The term "independently selected" is used herein to indicate that the designated groups, e.g., R, R' and R'', can be identical or different. A named R group will generally have the structure that is recognized in the art as corresponding to R groups having that name. For the purposes of illustration, representative R groups as enumerated above are defined herein. These definitions are intended to supplement and illustrate, not preclude, the definitions known to those of skill in the art.

The term "catalyst system" is defined to mean a catalyst precursor/activator pair. When "catalyst system" is used to describe such a pair before activation, it means the unactivated catalyst (precatalyst) together with an activator and, optionally, a co-activator. When it is used to describe such a pair after activation, it means the activated catalyst and the activator or other charge-balancing moiety.

The term "catalyst precursor" is also often referred to as precatalyst, catalyst, catalyst precursor, catalyst compound, transition metal compound, metallocene complex, and/or transition metal complex. These words are used interchangeably. Activator and cocatalyst are also used interchangeably. A scavenger is a compound that is typically added to facilitate oligomerization or polymerization by scavenging impurities. Some scavengers may also act as activators and may be referred to as co-activators. A co-activator, that is not a scavenger, may also be used in conjunction with an activator in order to form an active catalyst. In some embodiments a co-activator can be pre-mixed with the transition metal compound to form an alkylated transition metal compound, also referred to as an alkylated invention compound. The transition metal compound may be neutral as in a precatalyst, or a charged species with a counterion as in an activated catalyst system.

The terms "hydrocarbyl radical," "hydrocarbyl" and "hydrocarbyl group" are used interchangeably throughout this document. Likewise the terms "group," "radical," and "substituent" are also used interchangeably in this document. For purposes of this disclosure, "hydrocarbyl radical" is defined to be $C_1$-$C_{30}$ radicals, that may be linear, branched, or cyclic, and when cyclic, aromatic or non-aromatic, and include substituted hydrocarbyl radicals, as this term is defined below. When referring to a hydrogen substitutent, the terms "hydrogen" and "hydrogen radical" are used interchangeably.

Substituted hydrocarbyl radicals are radicals in which at least one hydrogen atom has been substituted with at least one functional group such as $NR^*_2$, $OR^*$, $SeR^*$, $TeR^*$, $PR^*_2$, $AsR^*_2$, $SbR^*_2$, $SR^*$, $BR^*_2$, $SiR^*_3$, $GeR^*_3$, $SnR^*_3$, $PbR^*_3$ and the like or where at least one non-hydrocarbon atom or group has been inserted within the hydrocarbyl radical, such as —O—, —S—, —Se—, —Te—, —N(R*)—, =N—, —P(R*)—, =P—, —As(R*)—, =As—, —Sb(R*)—=Sb—, —B(R*)—, =B—, —Si(R*)$_2$—, —Ge(R*)$_2$—, —Sn(R*)$_2$—, —Pb(R*)$_2$— and the like, where R* is independently a hydrocarbyl or halocarbyl radical, and two or more R* may join together to form a substituted or unsubstituted saturated, partially unsaturated or aromatic cyclic or polycyclic ring structure.

In some embodiments, the hydrocarbyl radical is independently selected from methyl, ethyl, ethenyl and isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, triacontynyl, butadienyl, pentadienyl, hexadienyl, heptadienyl, octadienyl, nonadienyl, and decadienyl.

Also included are isomers of saturated, partially unsaturated and aromatic cyclic and polycyclic structures wherein the hydrocarbyl radical may additionally be subjected to the types of substitutions described above. Examples include phenyl, methylphenyl, dimethylphenyl, ethylphenyl, diethylphenyl, propylphenyl, dipropylphenyl, benzyl, methylbenzyl, naphthyl, anthracenyl, cyclopentyl, cyclopentenyl, cyclohexyl, cyclohexenyl, methylcyclohexyl, cycloheptyl, cycloheptenyl, norbornyl, norbornenyl, adamantyl and the like.

For this disclosure, when a radical is listed, it indicates that radical type and all other radicals formed when that radical type is subjected to the substitutions defined above. Alkyl, alkenyl and alkynyl radicals listed include all isomers including where appropriate cyclic isomers, for example, butyl includes n-butyl, 2-methylpropyl, 1-methylpropyl, tert-butyl, and cyclobutyl (and analogous substituted cyclopropyls); pentyl includes n-pentyl, cyclopentyl, 1-methylbutyl, 2-methylbutyl, 3-methylbutyl, 1-ethylpropyl, and neopentyl (and analogous substituted cyclobutyls and cyclopropyls); butenyl includes E and Z forms of 1-butenyl, 2-butenyl, 3-butenyl, 1-methyl-1-propenyl, 1-methyl-2-propenyl, 2-methyl-1-propenyl and 2-methyl-2-propenyl (and cyclobutenyls and cyclopropenyls). Cyclic compound having substitutions include all isomer forms, for example, methylphenyl would include ortho-methylphenyl, meta-methylphenyl and para-methylphenyl; dimethylphenyl would include 2,3-dimethylphenyl, 2,4-dimethylphenyl, 2,5-dimethylphenyl, 2,6-methyldiphenyl, 3,4-dimethylphenyl, and 3,5-dimethylphenyl.

The term "halohydrocarbyl" is used herein to refer to any hydrocarbyl group in which one or more hydrocarbyl hydrogen atoms have been substituted with at least one halogen (e.g. F, Cl, Br, I) or halogen-containing group (e.g. $CF_3$). Halohydrocarbyl includes substituted halohydrocarbyl radicals. Suitable halohydrocarbyl groups include, for example, trifluoromethyl, pentafluorophenyl, dibromocyclohept-4-enyl and the like.

Substituted halohydrocarbyl radicals are radicals in which at least one halohydrocarbyl hydrogen or halogen atom has been substituted with at least one functional group such as $NR^*_2$, $OR^*$, $SeR^*$, $TeR^*$, $PR^*_2$, $AsR^*_2$, $SbR^*_2$, $SR^*$, $BR^*_2$, $SiR^*_3$, $GeR^*_3$, $SnR^*_3$, $PbR^*_3$ and the like or where at least one non-carbon atom or group has been inserted within the halohydrocarbyl radical such as —O—, —S—, —Se—, —Te—, —N(R*)—, =N—, —P(R*)—, =P—, —As(R*)—, =As—, —Sb(R*)—=Sb—, —B(R*)—, =B—, —Si(R*)$_2$—, —Ge(R*)$_2$—, —Sn(R*)$_2$—, —Pb(R*)$_2$— and the like, where R* is independently a hydrocarbyl or halohydrocarbyl radical provided that at least one halogen atom remains on the original halocarbyl radical. Additionally, two or more R* may join together to form a substituted or unsubstituted saturated, partially unsaturated or aromatic cyclic or polycyclic ring structure.

The term "silylhydrocarbyl" is used herein to refer to any branched or unbranched, saturated or unsaturated acyclic or acyclic hydrocarbon radical which has 1 to 30 carbon atoms and which has one or more hydrogen atoms replaced by a silicon atom. Where a silylhydrocarbyl radical is an $R'_2$ or $R''_2$ component of a $SiR'_2NR''_2$ group in the metallocene complex of the invention, the radical is bonded to the nitrogen atom through a carbon atom, rather than silicon atom. Suitable silylhydrocarbyl groups include, for example, 2-trimethylsilyleth-1-yl, 3-triethylsilylprop-1-yl and 2-dimethylsilylbut-1-yl.

The term "silylhalohydrocarbyl" is used herein to refer to any branched or unbranched, saturated or unsaturated acyclic or acyclic hydrocarbon radical has one or more hydrogen atoms replaced by a silicon atom and one or more hydrogen atoms replaced by a halogen atom. Where a silylhalohydrocarbyl radical is an $R'_2$ or $R''_2$ component of a $SiR'_2NR''_2$ group in the metallocene complex of the invention, the radical is bonded to the nitrogen atom through a carbon atom, rather than silicon atom in the case of R" or the radical is bonded to the silicon atom through a carbon atom, rather than silicon atom in the case of R'. Suitable silylhalohydrocarbyl groups include, for example, 1,1-difluoro-2-trimethylsilylethy-1-yl.

The term "germylcarbyl" is used herein to refer to any radical in which the germyl functionality is bonded directly to the indicated atom or atoms. Examples include $GeH_3$, $GeH_2R^*$, $GeHR^*_2$, $GeR^*3$, $GeH2(OR^*)$, $GeH(OR^*)2$, $Ge(OR^*)3$, $GeH2(NR^*2)$, $GeH(NR^*2)2$, $Ge(NR^*2)3$, and the like where R* is independently a hydrocarbyl or halocarbyl radical and two or more R* may join together to form a substituted or unsubstituted saturated, partially unsaturated or aromatic cyclic or polycyclic ring structure.

Metallocene Complex

In a preferred embodiment, this invention relates to a metallocene complex represented by the formula:

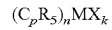

$(C_pR_5)_nMX_k$ where $C_p$ (each occurrence) is a cyclopentadienyl group having five R substituents; n is 1 or 2; M is a transition metal of valence m selected from Groups 4 to 11, preferably Groups 4 to 6, of the Periodic Table of Elements, such as titanium, zirconium and hafnium, preferably zirconium or hafnium; k is equal to m minus n; and the or each X substituent is a univalent anionic ligand, or two X substituents are joined and bound to the metal atom to form a metallocycle ring, or two X substituents are joined to form a chelating ligand, a diene ligand, or an alkylidene ligand.

More specifically, each X is, independently, a hydride radical, a hydrocarbyl radical, a substituted hydrocarbyl radical, a halocarbyl radical, a substituted halocarbyl radical, a silylcarbyl radical, substituted silylcarbyl radical, a germylcarbyl radical, or a substituted germylcarbyl radical, or both X are joined and bound to the metal atom to form a metallacycle ring containing from about 3 to about 20 carbon atoms; or both together can be an olefin, diolefin or aryne ligand; or when Lewis-acid activators, such as methylalumoxane, which are capable of donating an X ligand as described above to the transition metal component are used, each X may, independently, be a halogen, alkoxide, aryloxide, amide, phosphide or other univalent anionic ligand or both X can also be joined to form a anionic chelating ligand.

Suitable X groups include chloride, bromide, fluoride, methyl, benzyl, catecholate, diazazbutandiyl, tetramethylene, butadiene and methylidene.

Each of the R substituents on the or each cyclopentadienyl group is independently selected from hydrogen, a $C_1$ to $C_{30}$ substituted or unsubstituted hydrocarbyl, halohydrocarbyl, silylhydrocarbyl or silylhalohydrocarbyl group, and a $SiR'_2NR''_2$ group, wherein each of the two R' substituents is independently selected from $C_1$ to $C_{30}$ substituted or unsubstituted hydrocarbyl, halohydrocarbyl, silylhydrocarbyl or silylhalohydrocarbyl or where two R' substitutents may join together to form part of a monocyclic or polycyclic ring structure and each of the two R" substituents is independently selected from $C_2$ to $C_{30}$ substituted or unsubstituted hydrocarbyl, halohydrocarbyl, silylhydrocarbyl or silylhalohydrocarbyl or where two adjacent R" substituents may be joined to form part of a saturated, partially unsaturated or aromatic monocyclic or polycyclic ring structure, and where a R' and a R" may join together to form part of a monocyclic or polycyclic ring structure and; provided that at least one R substituent on the or one cyclopentadienyl group is $SiR'_2NR''_2$. Preferably, only one R substituent on each cyclopentadienyl group is $SiR'_2NR''_2$.

In one embodiment, said complex includes a single $SiR'_2NR''_2$ substituent and the remaining R substituents are hydrogen or methyl, preferably hydrogen.

In another embodiment, n is 2 and one R substituent on each cyclopentadienyl group is $SiR'_2NR''_2$ and the remaining R substituents on each cyclopentadienyl group are hydrogen or methyl, preferably hydrogen. In another embodiment, two adjacent R substituents on the or each cyclopentadienyl group may be joined to form part of a saturated, partially unsaturated or aromatic monocyclic or polycyclic ring structure, for example a benzene or a naphthalene ring. Moreover, one or the $C_p$ group may be bridged by a bridging group to another $C_p$ group, or a heteroatom containing group, where the bridging group replaces one R group on the $C_p$ group(s) or a hydrogen on a heteroatom containing group. Suitable bridging groups may be represented by the following formulae: $R_2C$, $R_2Si$, $R_2Ge$, $R_2CCR_2$, $R_2CCR_2CR_2$, $R_2CCR_2CR_2CR_2$, $RC=CR$, $RC=CRCR_2$, $R_2CCR=CRCR_2$, $RC=CRCR=CR$, $RC=CRCR_2$, $R_2CSiR_2$, $R_2SiSiR_2$, $R_2CSiR_2CR_2$, $R_2SiCR_2SiR_2$, $RC=CRSiR_2$, $R_2CGeR_2$, $R_2GeGeR_2$, $R_2CGeR_2CR_2$, $R_2GeCR_2GeR_2$, $R_2SiGeR_2$, $RC=CRGeR_2$, RB, $R_2C$—BR, $R_2C$—BR—$CR_2$, RN, RP, O, S, Se, $R_2C$—O—$CR_2$, $R_2CR_2C$—O—$CR_2CR_2$, $R_2C$—O—$CR_2CR_2$, $R_2C$—O—$CR=CR$, $R_2C$—S—$CR_2$, $R_2CR_2C$—S—$CR_2CR_2$, $R_2C$—S—$CR_2CR_2$, $R_2C$—S—$CR=CR$, $R_2C$—Se—$CR_2$, $R_2CR_2C$—Se—$CR_2CR_2$, $R_2C$—Se—$CR_2CR_2$, $R_2C$—Se—$CR=CR$, $R_2C$—N=CR, $R_2C$—NR—$CR_2$, $R_2C$—NR—$CR_2CR_2$, $R_2C$—NR—$CR=CR$, $R_2CR_2C$—NR—$CR_2CR_2$, $R_2C$—P=CR, and $R_2C$—PR—$CR_2$. Such bridging group replaces one R group on each Cp.

In addition, two adjacent R" substituents may be joined to form part of a saturated, partially unsaturated or aromatic monocyclic or polycyclic ring structure, such as a pyrrolidinyl or piperidinyl ring. Likewise two adjacent R' substituents may be joined to form part of a monocyclic or polycyclic silicon-containing ring structure. Further, an R" substitutent and an adjacent R' substituent may be joined to form part of a saturated monocyclic or polycyclic ring structure.

In another embodiment, each R' substituent is $C_1$ to $C_{12}$ hydrocarbyl, such as methyl.

In another embodiment, each R" substituent is $C_2$ to $C_{12}$ hydrocarbyl, such as iso-propyl.

Conveniently, the valence m is 3, 4, 5 or 6, n is 1 or 2 and k is 1, 2, 3, 4 or 5.

In another embodiment, the metallocene complex is represented by the formula I, II, III, or IV:

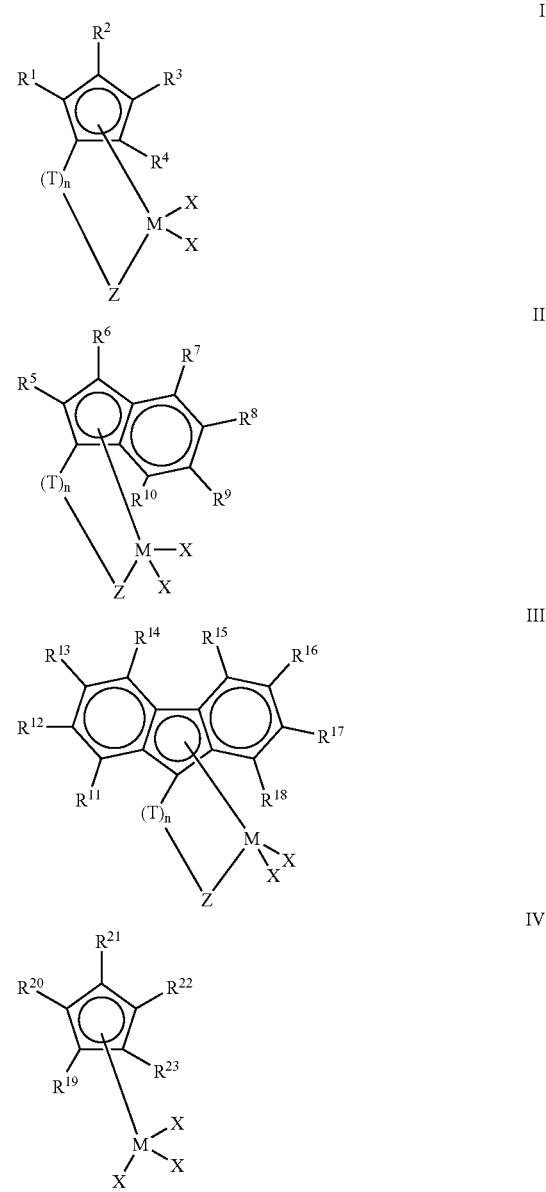

where M is a metal selected from Group 4, 5, 6, 7, 8, 9, 10 or 11 of the Periodic Table of the Elements, preferably M is a Group 4, 5 or 6 metal, preferably a Group 4 metal, preferably M is zirconium, titanium or hafnium, (the formulae above are represented as a four coordinate metal, in the event the metal has a coordination number of 3, then one X group is missing, if the metal has a coordination number of 5 or 6 then one or two more X groups are present, respectively); T is a bridging group, preferably T comprises a substituted or unsubstituted group 14 atom, preferably Si or C, preferably a dialky substituted silyl group and n is 0 or 1; X is a univalent anionic ligand, preferably a hydrocarbyl, substituted hydrocarbyl or halogen, preferably F, Br, Cl, or a C1 to C20 hydrocarbyl group; Z is a substituted or unsubstituted cyclopentadienyl group, a substituted or unsubstituted indenyl group, a substituted or unsubstituted fluorenyl group, or a heteroatom containing group, preferably Z is substituted with at least one Si—N group represented by the formula:

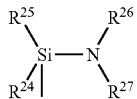

where $R^{24}$, $R^{25}$, $R^{26}$ and $R^{27}$ are, independently, substituted or unsubstituted hydrocarbyl groups and where $R^{26}$ and $R^{27}$ may optionally form a saturated or unsaturated ring structure, preferably $R^{24}$ and $R^{25}$ are independently a C1 to C12 hydrocarbyl, preferably methyl, ethyl, propyl or butyl, and preferably $R^{26}$ and $R^{27}$ form a substituted or unsubstituted ring, such as a pyrrolidinyl or piperidinyl ring; $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, and $R^{23}$ are, independently selected from the group consisting of hydrogen, substituted or unsubstituted hydrocarbyl, halohydrocarbyl, silylhydrocarbyl or silylhalohydrocarbyl groups, wherein two adjacent R substituents may form all or part of a saturated, partially unsaturated or aromatic monocyclic or polycyclic ring structure, provided that at least one of $R^1$, $R^2$, $R^3$, or $R^4$ in formula I, at least one of $R^5$, $R^6$, $R^7$, $R^8$, $R^9$, or $R^{10}$ in formula II, at least one of $R^{11}$, $R^{12}$, $R^{13}$, $R^{14}$, $R^{15}$, $R^{16}$, $R^{17}$ or $R^{18}$ in formula III, or at least one of $R^{19}$, $R^{20}$, $R^{21}$, $R^{22}$, or $R^{23}$ in formula IV is an Si—N group as defined above wherein at least one of $R^{26}$ and $R^{27}$ has at least 2 carbon aroms or wherein two adjacent $R^{24}$, $R^{25}$, $R^{26}$ and $R^{27}$ substituents may be joined to form part of a monocyclic or polycyclic ring structure.

In a preferred embodiment, in Formula I, II or III:

a) M is a group 4, 5 or 6 metal preferably a group 4 metal, preferably Zr, Hf or Ti, and or b) n is 1 and T is a silyl group substituted with two C1 to C12 hydrocarbyl groups, preferably a hydrocarbyl diyl, more preferably methyl, ethyl, propyl (including isopropyl), butyl (including isobutyl); and or c) each X is independently, a C1 to C20 hydrocarbyl group or a halogen, preferably Cl, Br, F, methyl, ethyl, propyl, butyl, benzyl, or hexyl; and or d) Z is substituted with two, three or four Si—N groups; and or e) two, three or four of $R^1$, $R^2$, $R^3$, or $R^4$ are Si—N groups, or two, three or four of $R^5$, $R^6$, $R^7$, $R^8$, $R^9$, or $R^{10}$ are Si—N groups, or two, three or four of $R^{11}$, $R^{12}$, $R^{13}$, $R^{14}$, $R^{15}$, $R^{16}$, $R^{17}$, or $R^{18}$ are Si—N groups; and or f) $R^{24}$ and $R^{25}$ are independently a C1 to C12 hydrocarbyl, preferably methyl, ethyl, propyl or butyl; and or g) $R^{26}$ and $R^{27}$ are, independently, a C1 to C12 hydrocarbyl group or form a substituted or unsubstituted pyrrolidinyl or piperidinyl ring In another preferred embodiment, in formula IV:

a) M is a group 4, 5 or 6 metal preferably a group 4 metal, preferably Zr, Hf or Ti, and or b) each X is independently, a C1 to C20 hydrocarbyl group or a halogen, preferably Cl, Br, F, methyl, ethyl, propyl, butyl, benzyl, or hexyl; and or c) two three or four of $R^{19}$, $R^{20}$, $R^{21}$, $R^{22}$, or $R^{23}$ are Si—N groups; and or d) $R^{24}$ and $R^{25}$ are independently a C1 to C12 hydrocarbyl, preferably methyl, ethyl, propyl or butyl; and or g) $R^{26}$ and $R^{27}$ are, independently, a C1 to C12 hydrocarbyl group or form a substituted or unsubstituted pyrrolidinyl or piperidinyl ring.

In another preferred embodiment, in Formula I, II or III, Z is a heteroatom containing group, preferably a group 15 heteroatom containing group, more preferably a C1 to C40 substituted heteroatom containing group, more preferably Z is an amido group such as dodecylamido, butylamido, benzylamido, phenethylamido, propylamido, dodecylphosphido, or adamantylamido.

In another embodiment, in any of formulae I, II, I or IV, $R^{25}$ and $R^{26}$ are joined to form a cyclic structure, preferably as represented by the following formula:

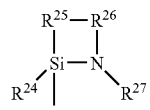

where $R^{24}$ is as defined above (except that $R^{24}$ and $R^{25}$ do not form a cyclic structure);

$R^{27}$ is as defined above (except that $R^{27}$ and $R^{26}$ do not form a cyclic structure);

$R^{25}$ and $R^{26}$ are each independently, a C1 to C20 hydrocarbyl, or a C1 to C20 substituted hydrocarbyl, preferably $R^{25}$ and $R^{26}$ together form a C3 to C6 hydrocarbyl or C3 to C6 substituted hydrocarbyl. In a preferred embodiment, $R^{25}$ and $R^{26}$ together form a C3 hydrocarbyl group.

In another preferred embodiment, the $NR''_2$ of the Si—N group forms a ring structure and/or $R^{26}$ and $R^{27}$ form a ring structure. Examples of $NR''_2$ forming a ring structure (and/or $R^{26}$ and $R^{27}$ forming a ring structure) are illustrated in the table below (for purposes of this table R' is defined below and is not defined as R' above):

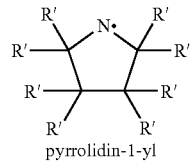

pyrrolidin-1-yl

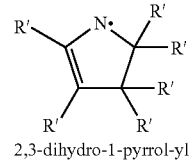

2,3-dihydro-1-pyrrol-yl

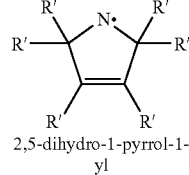

2,5-dihydro-1-pyrrol-1-yl

-continued
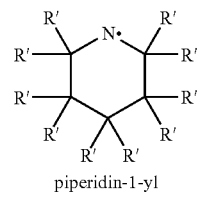
piperidin-1-yl
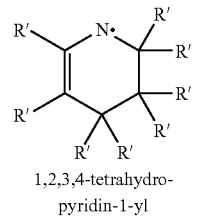
1,2,3,4-tetrahydro-pyridin-1-yl
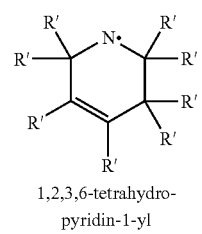
1,2,3,6-tetrahydro-pyridin-1-yl
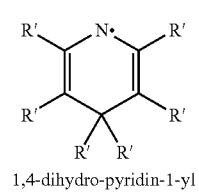
1,4-dihydro-pyridin-1-yl
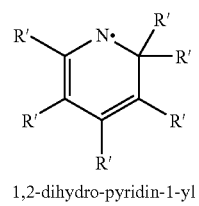
1,2-dihydro-pyridin-1-yl
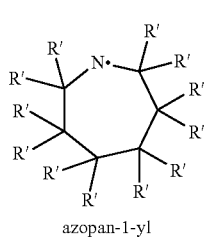
azopan-1-yl
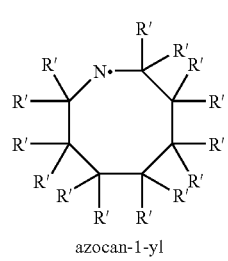
azocan-1-yl
-continued
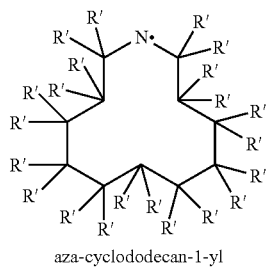
aza-cyclododecan-1-yl
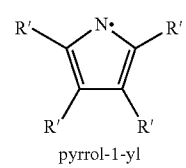
pyrrol-1-yl
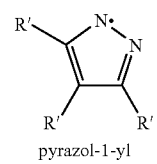
pyrazol-1-yl
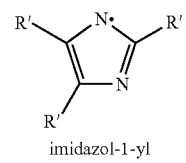
imidazol-1-yl
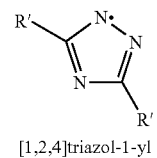
[1,2,4]triazol-1-yl
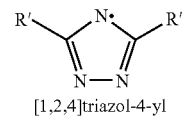
[1,2,4]triazol-4-yl
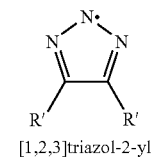
[1,2,3]triazol-2-yl
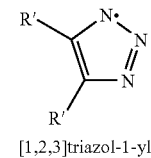
[1,2,3]triazol-1-yl
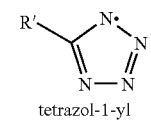
tetrazol-1-yl -continued
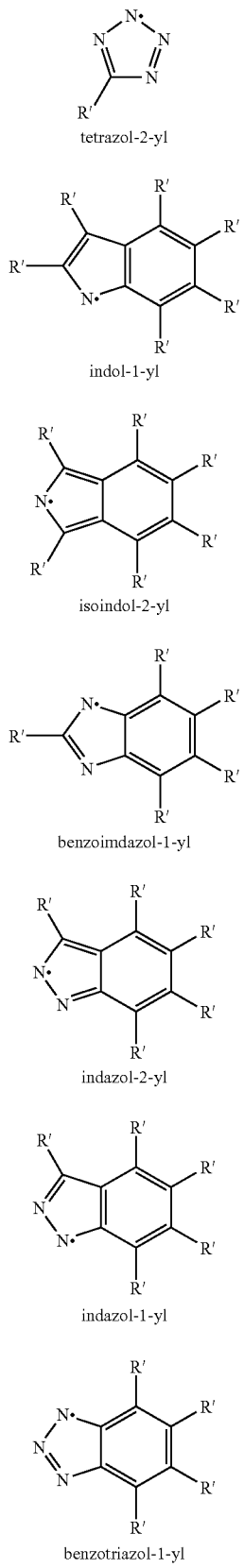
tetrazol-2-yl
indol-1-yl
isoindol-2-yl
benzoimdazol-1-yl
indazol-2-yl
indazol-1-yl
benzotriazol-1-yl
-continued
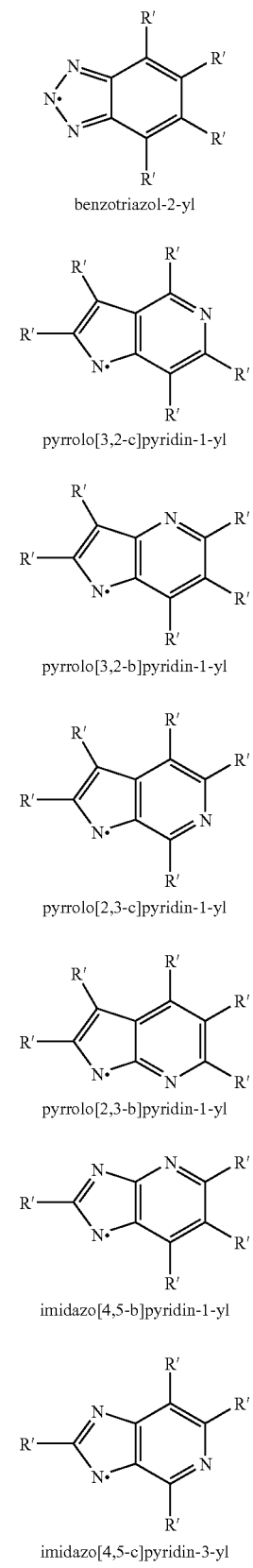
benzotriazol-2-yl
pyrrolo[3,2-c]pyridin-1-yl
pyrrolo[3,2-b]pyridin-1-yl
pyrrolo[2,3-c]pyridin-1-yl
pyrrolo[2,3-b]pyridin-1-yl
imidazo[4,5-b]pyridin-1-yl
imidazo[4,5-c]pyridin-3-yl -continued
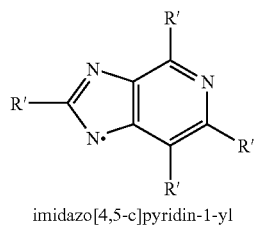
imidazo[4,5-c]pyridin-1-yl
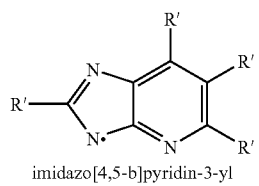
imidazo[4,5-b]pyridin-3-yl
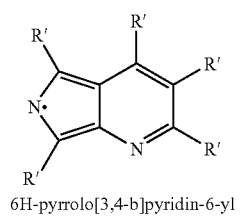
6H-pyrrolo[3,4-b]pyridin-6-yl
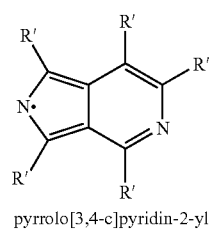
pyrrolo[3,4-c]pyridin-2-yl
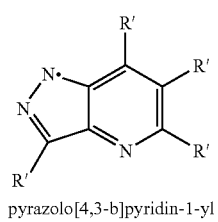
pyrazolo[4,3-b]pyridin-1-yl
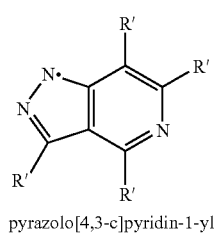
pyrazolo[4,3-c]pyridin-1-yl
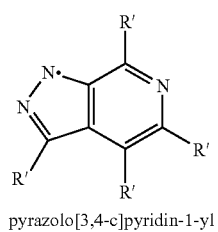
pyrazolo[3,4-c]pyridin-1-yl
-continued
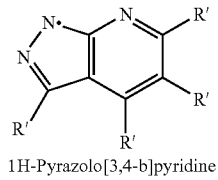
1H-Pyrazolo[3,4-b]pyridine
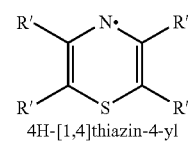
4H-[1,4]thiazin-4-yl
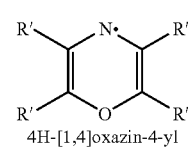
4H-[1,4]oxazin-4-yl
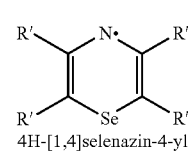
4H-[1,4]selenazin-4-yl
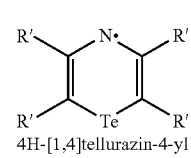
4H-[1,4]tellurazin-4-yl
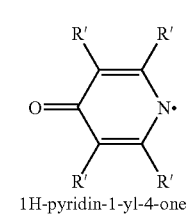
1H-pyridin-1-yl-4-one
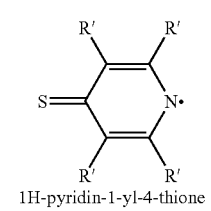
1H-pyridin-1-yl-4-thione
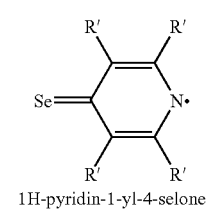
1H-pyridin-1-yl-4-selone
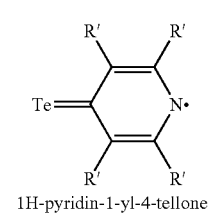
1H-pyridin-1-yl-4-tellone

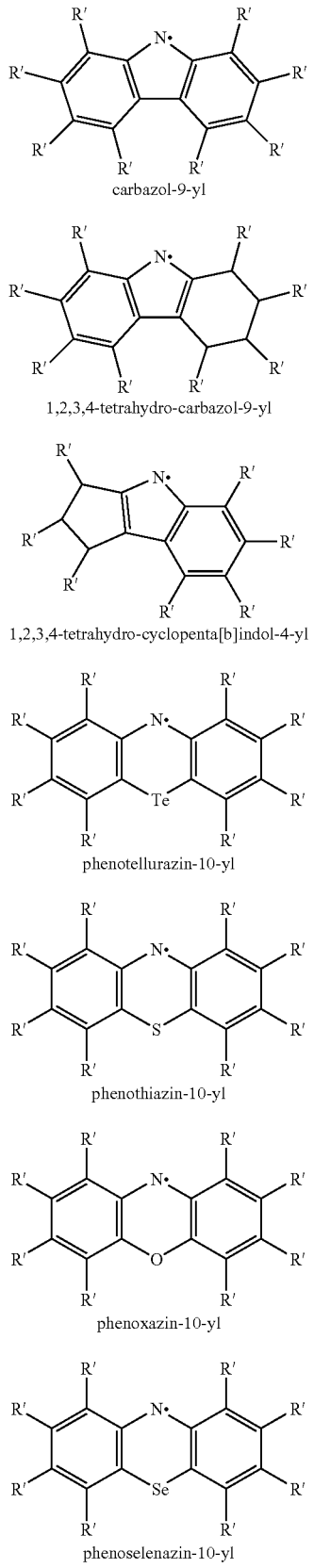

where the N. indicates the bond to the Si atom and each R' is selected from hydrogen, hydrocarbyl radicals, substituted hydrocarbyl radicals, halocarbyl radicals, substituted halocarbyl radicals, silylcarbyl radicals. Some invention embodiments select each R' from hydrogen or hydrocarbyl radicals including methyl, ethyl, ethenyl, ethynyl and all isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, and triacontynyl; from halocarbyls and all isomers of halocarbyls including perfluoropropyl, perfluorobutyl, perfluoropentyl, perfluorohexyl, perfluoroheptyl, perfluorooctyl, perfluorononyl, perfluorodecyl, perfluoroundecyl, perfluorododecyl, perfluorotridecyl, perfluorotetradecyl, perfluoropentadecyl, perfluorohexadecyl, perfluoroheptadecyl, perfluorooctadecyl, perfluorononadecyl, perfluoroeicosyl, perfluoroheneicosyl, perfluorodocosyl, perfluorotricosyl, perfluorotetracosyl, perfluoropentacosyl, perfluorohexacosyl, perfluoroheptacosyl, perfluorooctacosyl, perfluorononacosyl, perfluorotriacontyl, perfluorobutenyl, perfluorobutynyl, fluoropropyl, fluorobutyl, fluoropentyl, fluorohexyl, fluoroheptyl, fluorooctyl, fluorononyl, fluorodecyl, fluoroundecyl, fluorododecyl, fluorotridecyl, fluorotetradecyl, fluoropentadecyl, fluorohexadecyl, fluoroheptadecyl, fluorooctadecyl, fluorononadecyl, fluoroeicosyl, fluoroheneicosyl, fluorodocosyl, fluorotricosyl, fluorotetracosyl, fluoropentacosyl, fluorohexacosyl, fluoroheptacosyl, fluorooctacosyl, fluorononacosyl, fluorotriacontyl, difluorobutyl, trifluorobutyl, tetrafluorobutyl, pentafluorobutyl, hexafluorobutyl, heptafluorobutyl, octafluorobutyl; from substituted hydrocarbyl radicals and all isomers of substituted hydrocarbyl radicals including methoxypropyl, methoxybutyl, methoxypentyl, methoxyhexyl, methoxyheptyl, methoxyoctyl, methoxynonyl, methoxydecyl, methoxyundecyl, methoxydodecyl, methoxytridecyl, methoxytetradecyl, methoxypentadecyl, methoxyhexadecyl, methoxyheptadecyl, methoxyoctadecyl, methoxynonadecyl, methoxyeicosyl, methoxyheneicosyl, methoxydocosyl, methoxytricosyl, methoxytetracosyl, methoxypentacosyl, methoxyhexacosyl, methoxyheptacosyl, methoxyoctacosyl, methoxynonacosyl, methoxytriacontyl, butoxypropyl, butoxybutyl, butoxypentyl, butoxyhexyl, butoxyheptyl, butoxyoctyl, butoxynonyl, butoxydecyl, butoxyundecyl, butoxydodecyl, butoxytridecyl, butoxytetradecyl, butoxypentadecyl, butoxyhexadecyl, butoxyheptadecyl, butoxyoctadecyl, butoxynonadecyl, butoxyeicosyl, butoxyheneicosyl, butoxydocosyl, butoxytricosyl, butoxytetracosyl, butoxypentacosyl, butoxyhexacosyl, butoxyheptacosyl, butoxyoctacosyl, butoxynonacosyl, butoxytriacontyl, dimethylaminopropyl, dimethylaminobutyl, dimethylaminopentyl, dimethylaminohexyl, dimethylaminoheptyl, dimethylaminooctyl, dimethylaminononyl, dimethylaminodecyl, dimethylaminoundecyl, dimethylaminododecyl, dimethylaminotridecyl, dimethylaminotetradecyl, dimethylaminopentadecyl, dimethylaminohexadecyl, dimethylaminoheptadecyl, dimethylaminooctadecyl, dimethylaminononadecyl, dimethylaminoeicosyl, dimethylaminoheneicosyl, dimethylaminodocosyl, dimethylaminotricosyl, dimethylaminotetracosyl, dimethylaminopentacosyl, dimethylaminohexacosyl, dimethylaminoheptacosyl, dimethylaminooctacosyl, dimethylaminononacosyl, dimethylaminotriacontyl, trimethylsilylpropyl, trimethylsilylbutyl, trimethylsilylpentyl, trimethylsilylhexyl, trimethylsilylheptyl, trimethylsilyloctyl, trimethylsilylnonyl, trimethylsilyldecyl, trimethylsilylundecyl, trimethylsilyldodecyl, trimethylsilyltridecyl, trimethylsilyltetradecyl, trimethylsilylpentadecyl, trimethylsilylhexadecyl, trimethylsilylheptadecyl, trimethylsilyloctadecyl, trimethylsilylnonadecyl, trimethylsilyleicosyl, trimethylsilylheneicosyl, trimethylsilyldocosyl, trimethylsilyltricosyl, trimethylsilyltetracosyl, trimethylsilylpentacosyl, trimethylsilylhexacosyl, trimethylsilylheptacosyl, trimethylsilyloctacosyl, trimethylsilylnonacosyl, trimethylsilyltriacontyl and the like; from phenyl and all isomers of hydrocarbyl substituted phenyl including methylphenyl, dimethylphenyl, trimethylphenyl, tetramethylphenyl, pentamethylphenyl ethylphenyl, diethylphenyl, triethylphenyl, tetraethylphenyl, pentaethylphenyl, propylphenyl, dipropylphenyl, tripropylphenyl, tetrapropylphenyl, pentapropylphenyl butylphenyl, dibutylphenyl, tributylphenyl, tetrabutylphenyl, pentabutylphenyl, hexylphenyl, dihexylphenyl, trihexylphenyl, tetrahexylphenyl, pentahexylphenyl, dimethylethylphenyl, dimethylpropylphenyl, dimethylbutylphenyl, dimethylpentylphenyl, dimethylhexylphenyl, diethylmethylphenyl, diethylpropylphenyl, diethylbutylphenyl, diethylpentylphenyl, diethylhexylphenyl, dipropylmethylphenyl, dipropylethylphenyl, dipropylbutylphenyl, dipropylpentylphenyl, dipropylhexylphenyl, dibutylmethylphenyl, dibutylethylphenyl, dibutylpropylphenyl, dibutylpentylphenyl, dibutylhexylphenyl, methylethylphenyl, methylpropylphenyl, methylbutylphenyl, methylpentylphenyl, methylhexylphenyl, ethylpropylphenyl, ethylbutylphenyl, ethylpentylphenyl, ethylhexylphenyl, propylbutylphenyl, propylpentylphenyl, propylhexylphenyl, butylpentylphenyl, butylhexylphenyl, trimethylsilylphenyl, trimethylgermylphenyl, trifluoromethylphenyl, bis(triflouromethyl)phenyl and the like; from all isomers of halo substituted phenyl (where halo is, independently, fluoro, chloro, bromo and iodo) including halophenyl, dihalophenyl, trihalophenyl, tetrahalophenyl, and pentahalophenyl; from all isomers of halo substituted hydrocarbyl substituted phenyl (where halo is, independently, fluoro, chloro, bromo and iodo) including halomethylphenyl, dihalomethylphenyl, trihalomethylphenyl, tetrahalomethylphenyl, haloethlyphenyl, dihaloethylphenyl, trihaloethylphenyl, tetrahaloethylphenyl, halopropylphenyl, dihalopropylphenyl, trihalopropylphenyl, tetrahalopropylphenyl, halobutylphenyl, dihalobutylphenyl, trihalobutylphenyl, tetrahalobutylphenyl, dihalodimethylphenyl, dihalo(trifluoromethyl)phenyl and the like; from all isomers of benzyl, and all isomers of hydrocarbyl substituted benzyl including methylbenzyl, dimethylbenzyl, trimethylbenzyl, tetramethylbenzyl, pentamethylbenzyl ethylbenzyl, diethylbenzyl, triethylbenzyl, tetraethylbenzyl, pentaethylbenzyl, propylbenzyl, dipropylbenzyl, tripropylbenzyl, tetrapropylbenzyl, pentapropylbenzyl butylbenzyl, dibutylbenzyl, tributylbenzyl, tetrabutylbenzyl, pentabutylbenzyl, hexylbenzyl, dihexylbenzyl, trihexylbenzyl, tetrahexylbenzyl, pentahexylbenzyl, dimethylethylbenzyl, dimethylpropylbenzyl, dimethylbutylbenzyl, dimethylpentylbenzyl, dimethylhexylbenzyl, diethylmethylbenzyl, diethylpropylbenzyl, diethylbutylbenzyl, diethylpentylbenzyl, diethylhexylbenzyl, dipropylmethylbenzyl, dipropylethylbenzyl, dipropylbutylbenzyl, dipropylpentylbenzyl, dipropylhexylbenzyl, dibutylmethylbenzyl, dibutylethylbenzyl, dibutylpropylbenzyl, dibutylpentylbenzyl, dibutylhexylbenzyl, methylethylbenzyl, methylpropylbenzyl, methylbutylbenzyl, methylpentylbenzyl, methylhexylbenzyl, ethylpropylbenzyl, ethylbutylbenzyl, ethylpentylbenzyl, ethylhexylbenzyl, propylbutylbenzyl, propylpentylbenzyl, propylhexylbenzyl, butylpentylbenzyl, butylhexylbenzyl, trimethylsilylbenzyl, bis(trimethylsilyl)benzyl, trimethylgermylbenzyl, diphenylmethyl and the like; from trihydrocarbyl-silyl, -germyl, -stannyl and -plumbyl including trimethylsilyl, trimethylgermyl, trimethylstannyl, trimethylplumbyl, triethylsilyl, triethylgermyl, dimethylethylsilyl, dimethylethylgermyl, diethylmethylsilyl, diethylmethylgermyl, triphenylsilyl, triphenylgermyl, and all isomers of tripropylsilyl, tripropylgermyl, tributylsilyl, tributylgermyl, tris(trifluormethyl)silyl, bis(perfluoromethyl)methylsilyl, and the like; from all isomers and hydrocarbyl substituted isomers of polycyclic arenyls including pyrenyl, aceanthrylenyl, acenaphthylene, acephenanthrylenyl, azulenyl biphenylenyl, chrysenyl, coronenyl, fluoranthenyl, fluorenyl, heptacenyl, heptalenyl, heptaphenyl, hexacenyl, hexaphenyl, as-indacenyl, s-indecenyl, indenyl, ovalenyl, pentacenyl, pentalenyl, pentaphenyl, perylenyl, phenalenyl, phenanthrenyl, picenyl, pleiadenyl, pyranhrenyl, rubicenyl, naphthacenyl, tetraphenylenyl, trinaphthylenyl, triphenylenyl, hexahelicenyl, naphthyl, anthracenyl, dibenza[a,b]anthracenyl, indanyl, acenaphthenyl, cholanthrenyl, aceanthrenyl, acephenanthrenyl, 1,2,3,4-tetrahydronapthalene, fullerenyl, and the like; from all isomers and hydrocarbyl substituted isomers of alicyclic monocyclic and polycyclic hydrocarbon rings including cyclopropyl, cyclobutyl, cyclopentyl, cyclohexyl, cyclohexenyl, cycloheptyl, cyclooctyl, cyclononyl, cyclodecyl, cycloundecyl, and cyclododecyl, dimethylcyclohexyl, norbornyl, norbornenyl, adamantyl, cubanyl, prismanyl, spiro[4,5]decanyl, and the like; from all isomers and hydrocarbyl substituted isomers of ring assemblies including biphenyl, bicyclopentyl, terphenyl, quatercyclohexanyl, binaphthyl, binorbornyl, phenyl-terphenyl, and the like; from all isomers and hydrocarbyl substituted isomers of bridged monocyclic and polycyclic arenyls including 1,1-diphenylmethano, 1,1-dinapthyletheno, and the like; from all isomers of heterocycles and hydrocarbyl substituted heterocycles including acridarsinyl, acridinyl, acridophosphinyl, 1H-acrindolinyl, anthrazinyl, anthyridinyl, arsanthridinyl, arsindolyl, arsindolizinyl, arsinolinyl, arsinolizinyl, benzofuranyl, carbazolyl, β-carbolinyl, chromenyl, thiochromenyl, cinnolinyl, furanyl, imidazolyl, indazolyl, indolyl, indolizinyl, isoarsindolyl, isoarsinolinyl, isobenzofuranyl, isochromenyl, isothiochromenyl, isoindolyl, isophosphindolyl, isophosphinolinyl, isoquinolinyl, isothiazolyl, isoxazolyl, naphthyridinyl, oxazolyl, perimidinyl, phenanthrazinyl, phenanthridinyl, phenanthrolinyl, phenazinyl, phosphanthridinyl, phosphindolyl, phosphindolizinyl, phosphinolizinyl, phthalazinyl, pteridinyl, phthaloperinyl, purinyl, pyranyl, thiopyranal, pyrazinyl, pyrazolyl, pyridazinyl, pyridinyl, pyrindinyl, pyrimidinyl, pyrrolyl, pyrrolizinyl, quinazolinyl, quindolinyl, 1H-quinindolinyl, quinolinyl, quinolizinyl, quinoxalinyl, selenophenyl, thebenidinyl, thiazolyl, thiophenyl, triphenodioxazinyl, triphenodithiazinyl, xanthenyl, chromanyl, thiochromanyl, imidazolidinyl, indolinyl, isochromanyl, isothiochromanyl, isoindolinyl, morpholinyl, piperazinyl, piperidinyl, pyrozolidinyl, pyrrolidinyl, quinuclidinyl, dimethylacridarsinyl, dimethylacridinyl, dimethylacridophosphinyl, dimethyl-1H-acrindolinyl, dimethylanthrazinyl, dimethylanthyridinyl, dimethylarsanthridinyl, dimethylarsindolyl, dimethylarsindolizinyl, dimethylarsinolinyl, dimethylarsinolizinyl, dibutylbenzofuranyl, dibutylcarbazolyl, dibutyl-β-carbolinyl, dibutylchromenyl, dibutylthiochromenyl, butylcinnolinyl, dibutylfuranyl, dimethylimidazolyl, dimethylindazolyl, dipropylindolyl, dipropylindolizinyl, dimethylisoarsindolyl, methylisoarsinolinyl, dimethylisobenzofuranyl, diphenylisochromenyl, dibutylisothiochromenyl, phenylisoindolyl, butylisophosphindolyl, dibutylisophosphinolinyl, dimethylisoquinolinyl, methylisothiazolyl, butylisoxazolyl, butylnaphthyridinyl, dimethyloxazolyl, methylphenylperimidinyl, tetrabutylphenanthrazinyl, propylphenanthridinyl, dibutylphenanthrolinyl, tetramethylphenazinyl, butylphosphanthridinyl, phenylphosphindolyl, dimethylphosphindolizinyl, methylphosphinolizinyl, dibutylphthalazinyl, trimethylpteridinyl, methylphthaloperinyl, dimethylpurinyl, dibutylpyranyl, dibutylthiopyranal, trimethylpyrazinyl, phenylpyrazolyl, dipropylpyridazinyl, dimethylpyridinyl, methylpropylpyrindinyl, triethylpyrimidinyl, dibutylpyrrolyl, diethylpyrrolizinyl, dibutylquinazolinyl, dibutylquindolinyl, dibutyl-1H-quinindolinyl, dimethylquinolinyl, propylquinolizinyl, methylquinoxalinyl, methylbutylselenophenyl, methylthebenidinyl, dimethylthiazolyl, trimethylthiophenyl, dibutyltriphenodioxazinyl, dibutyltriphenodithiazinyl, dibutylxanthenyl, trimethylchromanyl, dimethylthiochromanyl, dimethylimidazolidinyl, dimethylindolinyl, dibutylisochromanyl, dibutylisothiochromanyl, phenylisoindolinyl, dibutylmorpholinyl, dimethylpiperazinyl, dimethylpiperidinyl, dimethylpyrozolidinyl, dimethylpyrrolidinyl, bipyridyl, pyrido[2,1,6-de]quinolizinyl, hexamethylquinuclidinyl, 5,7-dioxa-6-phosphadibenzo[a,c]cycloheptene-6-oxide, 9-oxa-10-phosphaphenanthrene-10-oxide and the like. In some embodiments of the invention, it is preferred that each R' is selected from, hydrogen, methyl, ethyl, n-propyl, iso-propyl, n-butyl, sec-butyl, iso-butyl, tert-butyl, pentyl, hexyl, cyclohexyl, phenyl, diphenylmethyl, or trifluoromethyl. In some embodiments R' on adjacent atoms may join together to form a substituted or unsubstituted saturated, partially unsaturated or aromatic cyclic or polycyclic ring structure.

Representative metallocene complexes according to the invention include:

Bis[(N-pyrrolidinyldimethylsilyl)cyclopentadienyl] zirconium dichloride, ("Complex A");

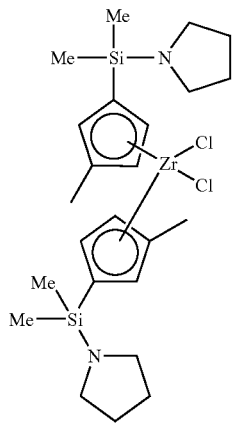

Bis[1-(N-pyrrolidinyldimethylsilyl)-3-methylcyclopentadienyl] zirconium

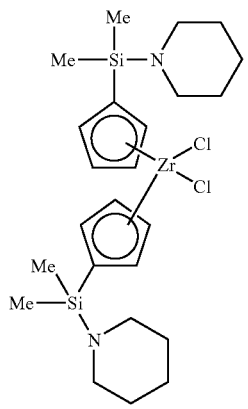

dichloride, ("Complex B");

Bis[(N-piperidinyldimethylsilyl)cyclopentadienyl] zirconium dichloride, ("Complex C");

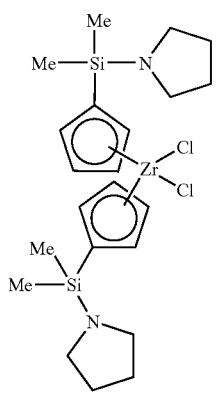

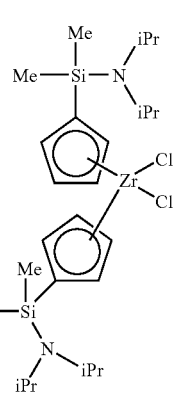

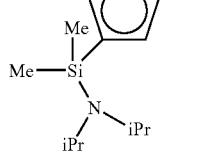

Bis[(N,N-diisopropylaminodimethylsilyl)cyclopentadienyl] zirconium dichloride, ("Complex D") and

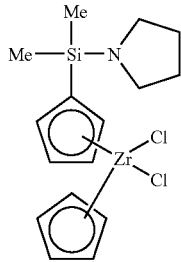

[(N-pyrrolidinyldimethylsilyl)cyclopentadienyl] [cyclopentadienyl] zirconium dichloride, ("Complex E").

In addition to Complexes A to E, preferred catalyst complexes according to this invention include:

Bis[(N-pyrrolidinyldimethylsilyl)cyclopentadienyl] zirconium dibromide,
Bis[1-(N-pyrrolidinyldimethylsilyl)-3-methylcyclopentadienyl] zirconium dibromide,
Bis[(N-piperidinyldimethylsilyl)cyclopentadienyl] zirconium dibromide,
Bis[(N,N-diisopropylaminodimethylsilyl)cyclopentadienyl] zirconium dibromide,
[(N-pyrrolidinyldimethylsilyl)cyclopentadienyl] [cyclopentadienyl] zirconium dibromide,
Bis[(N-pyrrolidinyldimethylsilyl)cyclopentadienyl] zirconium difluoride,
Bis[1-(N-pyrrolidinyldimethylsilyl)-3-methylcyclopentadienyl] zirconium difluoride,
Bis[(N-piperidinyldimethylsilyl)cyclopentadienyl] zirconium difluoride,
Bis[(N,N-diisopropylaminodimethylsilyl)cyclopentadienyl] zirconium difluoride,
[(N-pyrrolidinyldimethylsilyl)cyclopentadienyl] [cyclopentadienyl] zirconium difluoride,
Bis[(N-pyrrolidinyldimethylsilyl)cyclopentadienyl] zirconium dimethyl,
Bis[1-(N-pyrrolidinyldimethylsilyl)-3-methylcyclopentadienyl] zirconium dimethyl,
Bis[(N-piperidinyldimethylsilyl)cyclopentadienyl] zirconium dimethyl,
Bis[(N,N-diisopropylaminodimethylsilyl)cyclopentadienyl] zirconium dimethyl,
[(N-pyrrolidinyldimethylsilyl)cyclopentadienyl] [cyclopentadienyl] zirconium dimethyl,
Bis[(N-pyrrolidinyldimethylsilyl)cyclopentadienyl] zirconium diethyl,
Bis[1-(N-pyrrolidinyldimethylsilyl)-3-methylcyclopentadienyl] zirconium diethyl,
Bis[(N-piperidinyldimethylsilyl)cyclopentadienyl] zirconium diethyl,
Bis[(N,N-diisopropylaminodimethylsilyl)cyclopentadienyl] zirconium diethyl,
[(N-pyrrolidinyldimethylsilyl)cyclopentadienyl] [cyclopentadienyl] zirconium diethyl,
Bis[(N-pyrrolidinyldimethylsilyl)cyclopentadienyl] zirconium dimethoxide,
Bis[1-(N-pyrrolidinyldimethylsilyl)-3-methylcyclopentadienyl] zirconium dimethoxide,
Bis[(N-piperidinyldimethylsilyl)cyclopentadienyl] zirconium dimethoxide,
Bis[(N,N-diisopropylaminodimethylsilyl)cyclopentadienyl] zirconium dimethoxide,
[(N-pyrrolidinyldimethylsilyl)cyclopentadienyl] [cyclopentadienyl] zirconium dimethoxide,
Bis[(N-pyrrolidinyldimethylsilyl)cyclopentadienyl] zirconium diethoxide,
Bis[1-(N-pyrrolidinyldimethylsilyl)-3-methylcyclopentadienyl] zirconium diethoxide,
Bis[(N-piperidinyldimethylsilyl)cyclopentadienyl] zirconium diethoxide,
Bis[(N,N-diisopropylaminodimethylsilyl)cyclopentadienyl] zirconium diethoxide,
[(N-pyrrolidinyldimethylsilyl)cyclopentadienyl] [cyclopentadienyl] zirconium diethoxide,
Bis[(N-pyrrolidinyldimethylsilyl)cyclopentadienyl] hafnium dichloride,
Bis[1-(N-pyrrolidinyldimethylsilyl)-3-methylcyclopentadienyl] hafnium dichloride,
Bis[(N-piperidinyldimethylsilyl)cyclopentadienyl] hafnium dichloride,
Bis[(N,N-diisopropylaminodimethylsilyl)cyclopentadienyl] hafnium dichloride,
[(N-pyrrolidinyldimethylsilyl)cyclopentadienyl] [cyclopentadienyl] hafnium dichloride,
Bis[(N-pyrrolidinyldimethylsilyl)cyclopentadienyl] hafnium dibromide,
Bis[1-(N-pyrrolidinyldimethylsilyl)-3-methylcyclopentadienyl] hafnium dibromide,
Bis[(N-piperidinyldimethylsilyl)cyclopentadienyl] hafnium dibromide,
Bis[(N,N-diisopropylaminodimethylsilyl)cyclopentadienyl] hafnium dibromide,
[(N-pyrrolidinyldimethylsilyl)cyclopentadienyl] [cyclopentadienyl] hafnium dibromide,
Bis[(N-pyrrolidinyldimethylsilyl)cyclopentadienyl] hafnium difluoride,
Bis[1-(N-pyrrolidinyldimethylsilyl)-3-methylcyclopentadienyl] hafnium difluoride,
Bis[(N-piperidinyldimethylsilyl)cyclopentadienyl] hafnium difluoride,
Bis[(N,N-diisopropylaminodimethylsilyl)cyclopentadienyl] hafnium difluoride,
[(N-pyrrolidinyldimethylsilyl)cyclopentadienyl] [cyclopentadienyl] hafnium difluoride,
Bis[(N-pyrrolidinyldimethylsilyl)cyclopentadienyl] hafnium dimethyl,
Bis[1-(N-pyrrolidinyldimethylsilyl)-3-methylcyclopentadienyl] hafnium dimethyl,
Bis[(N-piperidinyldimethylsilyl)cyclopentadienyl] hafnium dimethyl,
Bis[(N,N-diisopropylaminodimethylsilyl)cyclopentadienyl] hafnium dimethyl,
[(N-pyrrolidinyldimethylsilyl)cyclopentadienyl] [cyclopentadienyl] hafnium dimethyl,
Bis[(N-pyrrolidinyldimethylsilyl)cyclopentadienyl] hafnium diethyl,
Bis[1-(N-pyrrolidinyldimethylsilyl)-3-methylcyclopentadienyl] hafnium diethyl,
Bis[(N-piperidinyldimethylsilyl)cyclopentadienyl] hafnium diethyl,
Bis[(N,N-diisopropylaminodimethylsilyl)cyclopentadienyl] hafnium diethyl,
[(N-pyrrolidinyldimethylsilyl)cyclopentadienyl] [cyclopentadienyl] hafnium diethyl,
Bis[(N-pyrrolidinyldimethylsilyl)cyclopentadienyl] hafnium dimethoxide,
Bis[1-(N-pyrrolidinyldimethylsilyl)-3-methylcyclopentadienyl] hafnium dimethoxide, Bis[(N-piperidinyldimethylsilyl)cyclopentadienyl] hafnium dimethoxide,
Bis[(N,N-diisopropylaminodimethylsilyl)cyclopentadienyl] hafnium dimethoxide,
[(N-pyrrolidinyldimethylsilyl)cyclopentadienyl] [cyclopentadienyl] hafnium dimethoxide,
Bis[(N-pyrrolidinyldimethylsilyl)cyclopentadienyl] hafnium diethoxide,
Bis[1-(N-pyrrolidinyldimethylsilyl)-3-methylcyclopentadienyl] hafnium diethoxide,
Bis[(N-piperidinyldimethylsilyl)cyclopentadienyl] hafnium diethoxide,
Bis[(N,N-diisopropylaminodimethylsilyl)cyclopentadienyl] hafnium diethoxide,
[(N-pyrrolidinyldimethylsilyl)cyclopentadienyl] [cyclopentadienyl] hafnium diethoxide,
Bis[(N,N-diiethylaminodimethylsilyl)cyclopentadienyl] zirconium dichloride, and
Bis[(N,N-diiethylaminodimethylsilyl)cyclopentadienyl] hafnium dichloride Another list of particularly preferred compounds includes all of the above compounds where "zirconium" is replaced with "titanium". Another list of particularly preferred compounds includes all of the above compounds where "dimethylsilyl" is replaced with "diethylsilyl". Another list of particularly preferred compounds includes all of the above compounds where "dimethylsilyl" is replaced with "diisobutylsilyl". Another list of particularly preferred compounds includes all of the above compounds where "dimethylsilyl" is replaced with "di-n-butylsilyl". Another list of particularly preferred compounds includes all of the above compounds where "dimethylsilyl" is replaced with "diisopropylsilyl". Another list of particularly preferred compounds includes all of the above compounds where "dimethylsilyl" is replaced with "dipropylsilyl". Another list of particularly preferred compounds includes all of the above compounds where "dimethylsilyl" is replaced with "diphenylsilyl". Another list of particularly preferred compounds includes all of the above compounds where "dimethylsilyl" is replaced with "methylethylsilyl". Another list of particularly preferred compounds includes all of the above compounds where "dimethylsilyl" is replaced with "methylpropylsilyl". Another list of particularly preferred compounds includes all of the above compounds where "dimethylsilyl" is replaced with "methylbutylsilyl". Another list of particularly preferred compounds includes all of the above compounds where "dimethylsilyl" is replaced with "methylphenylsilyl". Another list of particularly preferred compounds includes all of the above compounds where "dimethylsilyl" is replaced with "ethylbutylsilyl". Another list of particularly preferred compounds includes all of the above compounds where "dimethylsilyl" is replaced with "ethylphenylsilyl". Another list of particularly preferred compounds includes all of the above compounds where "dimethylsilyl" is replaced with "ethylpropylsilyl". Another list of particularly preferred compounds includes all of the above compounds where "dimethylsilyl" is replaced with "butylphenylsilyl". Another list of particularly preferred compounds includes all of the above compounds where "N,N-diisopropyl" is replaced with "N,N-dimethyl". Another list of particularly preferred compounds includes all of the above compounds where "N,N-diisopropyl" is replaced with "N,N-diethyl". Another list of particularly preferred compounds includes all of the above compounds where "N,N-diisopropyl" is replaced with "N,N-diisobutyl". Another list of particularly preferred compounds includes all of the above compounds where "N,N-diisopropyl" is replaced with "N,N-diphenyl". Another list of particularly preferred compounds includes all of the above compounds where "N,N-diisopropyl" is replaced with "N,N-di-n-butyl".

Methods of Making the Metallocene Complex

The metallocene complex of the invention is readily prepared by typical techniques such as reacting a cyclopentadienyl group (Cp) or a substituted cyclopentadienyl group (such as a methyl Cp) with an alkali metal (such as sodium), thereafter reacting the product with a halogenated silyl group such as (dimethylsilyldichloride) and thereafter reacting the product with a lithiated alkylamine, an alkylamine or an amine salt (such as $LiNR_2$ or $HNR_2$ where the R groups are methyl, ethyl, propyl (including isopropyl), butyl (including isobutyl), etc.) then reacting the product with n-butyllithium followed by a metal halide (such as zirconium tetrachloride or cyclopentadienyl zirconium trichloride).

Olefin Polymerization Catalyst System

The metallocene complex according to the invention is particularly useful as part of a catalyst system for polymerizing olefins. In such a catalyst system the metallocene complex, normally referred to a catalyst precursor, is combined with an activator or co-catalyst which increases the rate at which the metallocene complex polymerizes olefin monomers. An activator may also affect the molecular weight, degree of branching, comonomer content and other properties of the resultant polymer. Non-limiting activators include, for example, alumoxanes, aluminum alkyls and ionizing activators. Preferred activators typically include alumoxane compounds, modified alumoxane compounds, and ionizing anion precursor compounds that abstract one reactive, σ-bound, metal ligand (X) making the metal complex cationic and providing a charge-balancing noncoordinating or weakly coordinating anion.

In general, in the catalyst system of the invention the metallocene complex and the activator are combined in ratios of about 1:10,000 to about 10:1. When alumoxane or aluminum alkyl activators are used, the metallocene complex to activator molar ratio is from 1:5000 to 10:1, alternatively from 1:1000 to 10:1; alternatively, 1:500 to 2:1; or 1:300 to 1:1. When ionizing activators are used, the metallocene complex to activator molar ratio is from 10:1 to 1:10; 5:1 to 1:5; 2:1 to 1:2; or 1.2:1 to 1:1. Multiple activators may be used, including using mixtures of alumoxanes or aluminum alkyls with ionizing activators.

A stoichiometric activator can be either neutral or ionic. The terms ionic activator, and stoichiometric ionic activator can be used interchangeably. Likewise, the terms neutral stoichiometric activator, and Lewis acid activator can be used interchangeably.

Aluminoxane and Aluminum Alkyl Activators

In one embodiment, an alumoxane activator is utilized as an activator for the catalyst system useful in the invention. Alumoxanes are generally oligomeric compounds containing —Al($R^1$)—O— sub-units, where $R^1$ is an alkyl group. Examples of alumoxanes include methylalumoxane (MAO), modified methylalumoxane (MMAO), ethylalumoxane and isobutylalumoxane. Alkylalumoxanes and modified alkylalumoxanes are suitable as catalyst activators, particularly when the abstractable ligand is a halide, alkoxide or amide. Mixtures of different alumoxanes and modified alumoxanes may also be used.

It is recognized that alumoxane is not a discrete material. A typical alumoxane will contain free trisubstituted or trialkyl aluminum, bound trisubstituted or trialkyl aluminum, and alumoxane molecules of varying degree of oligomerization. Preferred methylalumoxanes contain lower levels of trimethylaluminum, which can be achieved by reaction of the trimethylaluminum with a Lewis base or by vacuum distillation of the trimethylaluminum or by any other means known in the art. It is also recognized that after reaction with the transition metal compound of the metallocene complex, some alumoxane molecules are in the anionic form and are considered "non-coordinating" anions.

For further description of alumoxanes, reference is directed to U.S. Pat. Nos. 4,665,208, 4,952,540, 5,041,584, 5,091,352, 5,206,199, 5,204,419, 4,874,734, 4,924,018, 4,908,463, 4,968,827, 5,329,032, 5,248,801, 5,235,081, 5,157,137, 5,103,031 and EP 0561 476 A1, EP 0 279 586 B1, EP 0 516 476 A, EP 0 594 218 A1 and WO 94/10180.

Alumoxanes may be produced by the hydrolysis of the respective trialkylaluminum compound. MMAO may be produced by the hydrolysis of trimethylaluminum and a higher trialkylaluminum such as triisobutylaluminum. MMAO's are generally more soluble in aliphatic solvents and more stable during storage. There are a variety of methods for preparing alumoxane and modified alumoxanes, non-limiting examples of which are described in U.S. Pat. Nos. 4,665,208, 4,952,540, 5,091,352, 5,206,199, 5,204,419, 4,874,734, 4,924,018, 4,908,463, 4,968,827, 5,308,815, 5,329,032, 5,248,801, 5,235,081, 5,157,137, 5,103,031, 5,391,793, 5,391,529, 5,693,838, 5,731,253, 5,731,451, 5,744,656, 5,847,177, 5,854,166, 5,856,256 and 5,939,346 and European publications EP-A-0 561 476, EP-B1-0 279 586, EP-A-0 594-218 and EP-B1-0 586 665, and PCT publications WO 94/10180 and WO 99/15534, all of which are herein fully incorporated by reference.

It may be preferable to use a visually clear methylalumoxane. A cloudy or gelled alumoxane can be filtered to produce a clear solution or clear alumoxane can be decanted from the cloudy solution. Another alumoxane is a modified methyl alumoxane (MMAO) cocatalyst type 3A (commercially available from Akzo Chemicals, Inc. under the trade name Modified Methylalumoxane type 3A).

Aluminum alkyl or organoaluminum compounds which may be utilized as activators (or scavengers) include trimethylaluminum, triethylaluminum, triisobutylaluminum, tri-n-hexylaluminum, tri-n-octylaluminum and the like.

Ionizing Activators

It is within the scope of this invention to use an ionizing or stoichiometric activator, neutral or ionic, such as tri (n-butyl) ammonium tetrakis (pentafluorophenyl) boron, a trisperfluorophenyl boron metalloid precursor or a trisperfluoronaphtyl boron metalloid precursor, polyhalogenated heteroborane anions (WO 98/43983), boric acid (U.S. Pat. No. 5,942,459) or combination thereof. It is also within the scope of this invention to use neutral or ionic activators alone or in combination with alumoxane or modified alumoxane activators.

Examples of neutral stoichiometric activators include tri-substituted boron, tellurium, aluminum, gallium and indium or mixtures thereof. The three substituent groups are each independently selected from alkyls, alkenyls, halogen, substituted alkyls, aryls, arylhalides, alkoxy and halides. Preferably, the three groups are independently selected from halogen, mono or multicyclic (including halosubstituted) aryls, alkyls, and alkenyl compounds and mixtures thereof, preferred are alkenyl groups having 1 to 20 carbon atoms, alkyl groups having 1 to 20 carbon atoms, alkoxy groups having 1 to 20 carbon atoms and aryl groups having 3 to 20 carbon atoms (including substituted aryls). More preferably, the three groups are alkyls having 1 to 4 carbon groups, phenyl, napthyl or mixtures thereof. Even more preferably, the three groups are halogenated, preferably fluorinated, aryl groups. Most preferably, the neutral stoichiometric activator is trisperfluorophenyl boron or trisperfluoronapthyl boron.

Ionic stoichiometric activator compounds may contain an active proton, or some other cation associated with, but not coordinated to, or only loosely coordinated to, the remaining ion of the ionizing compound. Such compounds and the like are described in European publications EP-A-0 570 982, EP-A-0 520 732, EP-A-0 495 375, EP-B1-0 500 944, EP-A-0 277 003 and EP-A-0 277 004, and U.S. Pat. Nos. 5,153,157, 5,198,401, 5,066,741, 5,206,197, 5,241,025, 5,384,299 and 5,502,124, all of which are herein fully incorporated by reference.

Ionic catalysts can be preparedly reacting a transition metal compound with a neutral Lewis acid, such as $B(C_6F_6)_3$, which upon reaction with the hydrolyzable ligand (X) of the transition metal compound forms an anion, such as $([B(C_6F_5)_3(X)]^-)$, which stabilizes the cationic transition metal species generated by the reaction. The catalysts can be, and preferably are, prepared with activator components which are ionic compounds or compositions. However preparation of activators utilizing neutral compounds is also contemplated by this invention.

Compounds useful as an activator component in the preparation of the ionic catalyst systems used in the process of this invention comprise a cation, which is preferably a Bronsted acid capable of donating a proton, and a compatible non-coordinating anion which anion is relatively large (bulky), capable of stabilizing the active catalyst species (the Group 4 cation) which is formed when the two compounds are combined and said anion will be sufficiently labile to be displaced by olefinic diolefinic and acetylenically unsaturated substrates or other neutral Lewis bases such as ethers, nitriles and the like. Two classes of compatible non-coordinating anions have been disclosed in EPA 277,003 and EPA 277,004 published 1988: 1) anionic coordination complexes comprising a plurality of lipophilic radicals covalently coordinated to and shielding a central charge-bearing metal or metalloid core, and 2) anions comprising a plurality of boron atoms such as carboranes, metallacarboranes and boranes.

In a preferred embodiment, the stoichiometric activators include a cation and an anion component, and may be represented by the following formula:

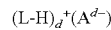

$(L-H)_d^+(A^{d-})$ wherein L is an neutral Lewis base; H is hydrogen; $(L-H)^+$ is a Bronsted acid and $A^{d-}$ is a non-coordinating anion having the charge d, where d is an integer from 1 to 3.

The cation component, $(L-H)_d^+$ may include Bronsted acids such as protons or protonated Lewis bases or reducible Lewis acids capable of protonating or abstracting a moiety, such as an alkyl or aryl, from the bulky ligand metallocene containing transition metal catalyst precursor, resulting in a cationic transition metal species.

The activating cation $(L-H)_d^+$ may be a Bronsted acid, capable of donating a proton to the transition metal catalytic precursor resulting in a transition metal cation, including ammoniums, oxoniums, phosphoniums, silyliums, and mixtures thereof, preferably ammoniums of methylamine, aniline, dimethylamine, diethylamine, N-methylaniline, diphenylamine, trimethylamine, triethylamine, N,N-dimethylaniline, methyldiphenylamine, pyridine, p-bromo N,N-dimethylaniline, p-nitro-N,N-dimethylaniline, phosphoniums from triethylphosphine, triphenylphosphine, and diphenylphosphine, oxomiuns from ethers such as dimethyl ether diethyl ether, tetrahydrofuran and dioxane, sulfoniums from thioethers, such as diethyl thioethers and tetrahydrothiophene, and mixtures thereof. The activating cation $(L-H)_d^+$ may also be a moiety such as silver, tropylium, carbeniums, ferroceniums and mixtures, preferably carboniums and ferroceniums. Most preferably $(L-H)_d^+$ is triphenyl carbonium.

The anion component $A^{d-}$ may include a compound having the formula $[N^{k+}Q_n]^{d-}$ wherein k is an integer from 1 to 3; n is an integer from 2-6; n−k=d; N is an element selected from Group 13 of the Periodic Table of the Elements, preferably boron or aluminum, and Q is independently a hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q having up to 20 carbon atoms with the proviso that in not more than 1 occurrence is Q a halide. Preferably, each Q is a fluorinated hydrocarbyl group having 1 to 20 carbon atoms, more preferably each Q is a fluorinated aryl group, and most preferably each Q is a pentafluoryl aryl group. Examples of suitable $A^{d-}$ also include diboron compounds as disclosed in U.S. Pat. No. 5,447,895, which is fully incorporated herein by reference.

Illustrative, but not limiting examples of boron compounds which may be used as an activating cocatalyst in the preparation of the improved catalysts of this invention are tri-substituted ammonium salts such as: trimethylammonium tetraphenylborate, triethylammonium tetraphenylborate, tripropylammonium tetraphenylborate, tri(n-butyl)ammonium tetraphenylborate, tri(t-butyl)ammonium tetraphenylborate, N,N-dimethylanilinium tetraphenylborate, N,N-diethylanilinium tetraphenylborate, N,N-dimethyl-(2,4,6-trimethylanilinium) tetraphenylborate, tropillium tetraphenylborate, triphenylcarbenium tetraphenylborate, triphenylphosphonium tetraphenylborate triethylsilylium tetraphenylborate, benzene(diazonium)tetraphenylborate, trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium) tetrakis(pentafluorophenyl)borate, tropillium tetrakis(pentafluorophenyl)borate, triphenylcarbenium tetrakis(pentafluorophenyl)borate, triphenylphosphonium tetrakis(pentafluorophenyl)borate, triethylsilylium tetrakis(pentafluorophenyl)borate, benzene(diazonium) tetrakis(pentafluorophenyl)borate, trimethylammonium tetrakis-(2,3,4,6-tetrafluorophenyl) borate, triethylammonium tetrakis-(2,3,4,6-tetrafluorophenyl)borate, tripropylammonium tetrakis-(2,3,4,6-tetrafluorophenyl)borate, tri(n-butyl) ammonium tetrakis-(2,3,4,6-tetrafluoro-phenyl)borate, dimethyl(t-butyl)ammonium tetrakis-(2,3,4,6-tetrafluorophenyl)borate, N,N-dimethylanilinium tetrakis-(2,3,4,6-tetrafluorophenyl)borate, N,N-diethylanilinium tetrakis-(2,3,4,6-tetrafluorophenyl)borate, N,N-dimethyl-(2,4,6-trimethylanilinium) tetrakis-(2,3,4,6-tetrafluorophenyl) borate, tropillium tetrakis-(2,3,4,6-tetrafluorophenyl)borate, triphenylcarbenium tetrakis-(2,3,4,6-tetrafluorophenyl)borate, triphenylphosphonium tetrakis-(2,3,4,6-tetrafluorophenyl)borate, triethylsilylium tetrakis-(2,3,4,6-tetrafluorophenyl)borate, benzene(diazonium) tetrakis-(2,3,4,6-tetrafluorophenyl)borate, trimethylammonium tetrakis (perfluoronapthyl)borate, triethylammonium tetrakis (perfluoronapthyl)borate, tripropylammonium tetrakis (perfluoronapthyl)borate, tri(n-butyl)ammonium tetrakis (perfluoronapthyl)borate, tri(t-butyl)ammonium tetrakis (perfluoronapthyl)borate, N,N-dimethylanilinium tetrakis (perfluoronapthyl)borate, N,N-diethylanilinium tetrakis (perfluoronapthyl)borate, N,N-dimethyl-(2,4,6-trimethylanilinium) tetrakis(perfluoronapthyl)borate, tropillium tetrakis(perfluoronapthyl)borate, triphenylcarbenium tetrakis(perfluoronapthyl)borate, triphenylphosphonium tetrakis(perfluoronapthyl)borate, triethylsilylium tetrakis(perfluoronapthyl)borate, benzene(diazonium) tetrakis(perfluoronapthyl)borate, trimethylammonium tetrakis (perfluorobiphenyl)borate, triethylammonium tetrakis (perfluorobiphenyl)borate, tripropylammonium tetrakis (perfluorobiphenyl)borate, tri(n-butyl)ammonium tetrakis (perfluorobiphenyl)borate, tri(t-butyl)ammonium tetrakis (perfluorobiphenyl)borate, N,N-dimethylanilinium tetrakis (perfluorobiphenyl)borate, N,N-diethylanilinium tetrakis (perfluorobiphenyl)borate, N,N-dimethyl-(2,4,6-trimethylanilinium) tetrakis(perfluorobiphenyl)borate, tropillium tetrakis(perfluorobiphenyl)borate, triphenylcarbenium tetrakis(perfluorobiphenyl)borate, triphenylphosphonium tetrakis(perfluorobiphenyl)borate, triethylsilylium tetrakis(perfluorobiphenyl)borate, benzene(diazonium) tetrakis(perfluorobiphenyl)borate, trimethylammonium tetrakis(3,5-bis(trifluoromethyl)phenyl)borate, triethylammonium tetrakis(3,5-bis(trifluoromethyl)phenyl)borate, tripropylammonium tetrakis(3,5-bis(trifluoromethyl)phenyl)borate, tri(n-butyl)ammonium tetrakis(3,5-bis(trifluoromethyl)phenyl)borate, tri(t-butyl)ammonium tetrakis(3,5-bis(trifluoromethyl)phenyl)borate, N,N-dimethylanilinium tetrakis(3,5-bis(trifluoromethyl)phenyl)borate, N,N-diethylanilinium tetrakis(3,5-bis(trifluoromethyl)phenyl)borate, N,N-dimethyl-(2,4,6-trimethylanilinium) tetrakis(3,5-bis(trifluoromethyl)phenyl)borate, tropillium tetrakis(3,5-bis(trifluoromethyl)phenyl)borate, triphenylcarbenium tetrakis(3,5-bis(trifluoromethyl)phenyl)borate, triphenylphosphonium tetrakis(3,5-bis(trifluoromethyl)phenyl)borate, triethylsilylium tetrakis(3,5-bis(trifluoromethyl)phenyl)borate, benzene(diazonium) tetrakis(3,5-bis(trifluoromethyl)phenyl)borate, and dialkyl ammonium salts such as: di-(i-propyl)ammonium tetrakis(pentafluorophenyl)borate, and dicyclohexylammonium tetrakis(pentafluorophenyl)borate; and additional tri-substituted phosphonium salts such as tri(o-tolyl)phosphonium tetrakis(pentafluorophenyl) borate, and tri(2,6-dimethylphenyl)phosphonium tetrakis (pentafluorophenyl)borate.

Most preferably, the ionic stoichiometric activator $(L-H)_d^+ (A^{d-})$ is N,N-dimethylanilinium tetra(perfluorophenyl)borate, N,N-dimethylanilinium tetrakis(perfluoronapthyl)borate, N,N-dimethylanilinium tetrakis(perfluorobiphenyl)borate, N,N-dimethylanilinium tetrakis(3,5-bis (trifluoromethyl)phenyl)borate, triphenylcarbenium tetrakis (perfluoronapthyl)borate, triphenylcarbenium tetrakis (perfluorobiphenyl)borate, triphenylcarbenium tetrakis(3,5-bis(trifluoromethyl)phenyl)borate, or triphenylcarbenium tetra(perfluorophenyl)borate.

In one embodiment, an activation method using ionizing ionic compounds not containing an active proton but capable of producing a bulky ligand metallocene catalyst cation and their non-coordinating anion is also contemplated, and is described in EP-A-0 426 637, EP-A-0 573 403 and U.S. Pat. No. 5,387,568, which are all herein incorporated by reference.

The term "non-coordinating anion" (NCA) is defined to mean an anion either that does not coordinate to the catalyst metal cation or that does coordinate to the metal cation, but only weakly. An NCA coordinates weakly enough that a neutral Lewis base, such as an olefinically or acetylenically unsaturated monomer, can displace it from the catalyst center.

"Compatible" non-coordinating anions are those which are not degraded to neutrality when the initially formed complex decomposes. Further, the anion will not transfer an anionic substituent or fragment to the cation so as to cause it to form a neutral four coordinate metallocene compound and a neutral by-product from the anion. Non-coordinating anions useful in accordance with this invention are those that are compatible, stabilize the metallocene cation in the sense of balancing its ionic charge at +1, yet retain sufficient lability to permit displacement by an ethylenically or acetylenically unsaturated monomer during polymerization. These types of cocatalysts sometimes use tri-isobutyl aluminum or tri-octyl aluminum as a scavenger.

Any metal or metalloid that can form a compatible, weakly coordinating complex may be used or contained in the non-coordinating anion. Suitable metals include, but are not limited to, aluminum, gold, and platinum. Suitable metalloids include, but are not limited to, boron, aluminum, phosphorus, and silicon.

The catalyst system of the invention can also employ cocatalyst compounds or activator compounds that are initially neutral Lewis acids but form a cationic metal complex and a noncoordinating anion, or a zwitterionic complex upon reaction with the invention compounds. For example, tris(pentafluorophenyl) boron or aluminum can act to abstract a hydrocarbyl or hydride ligand to yield a cationic metal complex and stabilizing noncoordinating anion, see EP-A-0 427 697 and EP-A-0 520 732 for illustrations of analogous Group-4 metallocene compounds. Also, see the methods and compounds of EP-A-0 495 375. For formation of zwitterionic complexes using analogous Group 4 compounds, see U.S. Pat. Nos. 5,624,878; 5,486,632; and 5,527,929.

When the cations of noncoordinating anion precursors are Bronsted acids such as protons or protonated Lewis bases (excluding water), or reducible Lewis acids such as ferrocenium or silver cations, or alkali or alkaline earth metal cations such as those of sodium, magnesium or lithium, the catalyst-precursor-to-activator molar ratio may be any ratio. Combinations of the described activator compounds may also be used for activation. For example, tris(perfluorophenyl) boron can be used with methylalumoxane.

Additional Activators

Other activators include those described in PCT Publication No. WO 98/07515, such as tris (2,2', 2"-nonafluorobiphenyl) fluoroaluminate, which publication is fully incorporated herein by reference. Combinations of activators are also contemplated by the invention, for example, alumoxanes and ionizing activators in combinations, see for example, EP-B1 0 573 120, PCT Publication Nos WO 94/07928 and WO 95/14044 and U.S. Pat. Nos. 5,153,157 and 5,453,410 all of which are herein fully incorporated by reference.

Other suitable activators are disclosed in WO 98/09996, incorporated herein by reference, which describes activating bulky ligand metallocene catalyst compounds with perchlorates, periodates and iodates including their hydrates. WO 98/30602 and WO 98/30603, incorporated by reference, describe the use of lithium (2,2'-bisphenyl-ditrimethylsilicate).4THF as an activator for a bulky ligand metallocene catalyst compound. WO 99/18135, incorporated herein by reference, describes the use of organo-boron-aluminum acitvators. EP-B1-0 781 299 describes using a silylium salt in combination with a non-coordinating compatible anion.

Also, methods of activation such as using radiation (see EP-B1-0 615 981 herein incorporated by reference), electrochemical oxidation, and the like are also contemplated as activating methods for the purposes of rendering the neutral bulky ligand metallocene catalyst compound or precursor to a bulky ligand metallocene cation capable of polymerizing olefins. Other activators or methods for activating a bulky ligand metallocene catalyst compound are described in for example, U.S. Pat. Nos. 5,849,852, 5,859,653 and 5,869,723 and WO 98/32775, WO 99/42467 (dioctadecylmethylammonium-bis(tris(pentafluorophenyl)borane) benzimidazolide), which are herein incorporated by reference.

Another suitable ion forming, activating cocatalyst comprises a salt of a cationic oxidizing agent and a noncoordinating, compatible anion represented by the formula:

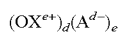

wherein $OX^{e+}$ is a cationic oxidizing agent having a charge of e+; e is an integer from 1 to 3; and $A^-$, and d are as previously defined. Examples of cationic oxidizing agents include: ferrocenium, hydrocarbyl-substituted ferrocenium, $Ag^+$, or $Pb^{+2}$. Preferred embodiments of $A^{d-}$ are those anions previously defined with respect to the Bronsted acid containing activators, especially tetrakis(pentafluorophenyl)borate.

Activator Combinations

It within the scope of this invention that metallocene complex of the invention can be combined with one or more activators or activation methods described above. For example, a combination of activators have been described in U.S. Pat. Nos. 5,153,157 and 5,453,410, European publication EP-B1 0 573 120, and PCT publications WO 94/07928 and WO 95/14044. These documents all discuss the use of an alumoxane in combination with an ionizing activator.

Catalyst Supports

The catalyst system of this invention may include a support material or carrier. For example, the metallocene complex and/or one or more activators may be deposited on, contacted with, vaporized with, bonded to, or incorporated within, adsorbed or absorbed in, or on, one or more supports or carriers.

The support material is any of the conventional support materials. Preferably the supported material is a porous support material, for example, talc, inorganic oxides and inorganic chlorides. Other support materials include resinous support materials such as polystyrene, functionalized or crosslinked organic supports, such as polystyrene divinyl benzene polyolefins or polymeric compounds, zeolites, clays, or any other organic or inorganic support material and the like, or mixtures thereof.

The preferred support materials are inorganic oxides that include those Group 2, 3, 4, 5, 13 or 14 metal oxides. The preferred supports include silica, which may or may not be dehydrated, fumed silica, alumina (WO 99/60033), silica-alumina and mixtures thereof. Other useful supports include magnesia, titania, zirconia, magnesium chloride (U.S. Pat. No. 5,965,477), montmorillonite (European Patent EP-B1 0 511 665), phyllosilicate, zeolites, talc, clays (U.S. Pat. No. 6,034,187) and the like. Also, combinations of these support materials may be used, for example, silica-chromium, silica-alumina, silica-titania and the like. Additional support materials may include those porous acrylic polymers described in EP 0 767 184 B1, which is incorporated herein by reference.

Other support materials include nanocomposites as described in PCT WO 99/47598, aerogels as described in WO 99/48605, spherulites as described in U.S. Pat. No. 5,972,510 and polymeric beads as described in WO 99/50311, which are all herein incorporated by reference.

It is preferred that the support material, most preferably an inorganic oxide, has a surface area in the range of from about 10 to about 700 m$^2$/g, pore volume in the range of from about 0.1 to about 4.0 cc/g and average particle size in the range of from about 5 to about 500 μm. More preferably, the surface area of the support material is in the range of from about 50 to about 500 m$^2$/g, pore volume of from about 0.5 to about 3.5 cc/g and average particle size of from about 10 to about 200 μm. Most preferably the surface area of the support material is in the range is from about 100 to about 400 m$^2$/g, pore volume from about 0.8 to about 3.0 cc/g and average particle size is from about 5 to about 100 μm. The average pore size of the carrier useful in the invention typically has pore size in the range of from 10 to 1000 Å, preferably 50 to about 500 Å, and most preferably 75 to about 350 Å.

As is well known in the art, the catalyst components, that is the metallocene complex and the activator, may also be supported together on one inert support, or the components may be independently placed on two inert supports and subsequently mixed. Of the two methods, the former is preferred.

In another embodiment the support may comprise one or more types of support material which may be treated differently. For example one could use two different silicas that had different pore volumes or had been calcined at different temperatures. Likewise one could use a silica that had been treated with a scavenger or other additive and a silica that had not.

Monomers

The catalyst system described herein may be used for the polymerization of one or more of monomers. Typical monomers include monomers having from 2 to 30 carbon atoms, preferably 2-12 carbon atoms, and more preferably 2 to 8 carbon atoms. Useful monomers include linear, branched or cyclic olefins, especially linear branched or cyclic alpha-olefins; linear, branched or cyclic diolefins, such as linear branched or cyclic alpha-omega olefins; and linear, branched or cyclic polyenes.

Preferred linear alpha-olefins include $C_3$ to $C_8$ alpha-olefins, more preferably propylene, 1-butene, 1-hexene, and 1-octene, even more preferably propylene or 1-butene. Preferred branched alpha-olefins include 4-methyl-1-pentene, 3-methyl-1-pentene, and 3,5,5-trimethyl-1-hexene, 5-ethyl-1-nonene. Preferred aromatic-group-containing monomers contain up to 30 carbon atoms. Suitable aromatic-group-containing monomers comprise at least one aromatic structure, preferably from one to three, more preferably a phenyl, indenyl, fluorenyl, or naphthyl moiety. The aromatic-group-containing monomer further comprises at least one polymerizable double bond such that after polymerization, the aromatic structure will be pendant from the polymer backbone. The aromatic-group containing monomer may further be substituted with one or more hydrocarbyl groups including but not limited to $C_1$ to $C_{10}$ alkyl groups. Additionally two adjacent substitutions may be joined to form a ring structure. Preferred aromatic-group-containing monomers contain at least one aromatic structure appended to a polymerizable olefinic moiety. Particularly preferred aromatic monomers include styrene, alpha-methylstyrene, para-alkyl-styrenes, vinyltoluenes, vinylnaphthalene, allyl benzene, and indene, especially styrene, paramethyl styrene, 4-phenyl-1-butene and allyl benzene.

Non aromatic cyclic group containing monomers can also be used. These monomers can contain up to 30 carbon atoms. Suitable non-aromatic cyclic group containing monomers preferably have at least one polymerizable olefinic group that is either pendant on the cyclic structure or is part of the cyclic structure. The cyclic structure may also be further substituted by one or more hydrocarbyl groups such as, but not limited to, $C_1$ to $C_{10}$ alkyl groups. Preferred non-aromatic cyclic group containing monomers include vinylcyclohexane, vinylcyclohexene, vinylnorbornene, ethylidene norbornene, cyclopentadiene, cyclopentene, cyclohexene, cyclobutene, vinyladamantane and the like.

Diolefin monomers useful in this invention include any hydrocarbon structure, preferably $C_4$ to $C_{30}$, having at least two unsaturated bonds, wherein at least two of the unsaturated bonds are readily incorporated into a polymer by either a stereospecific or a non-stereospecific catalyst(s). It is further preferred that the diolefin monomers be selected from alpha, omega-diene monomers (i.e. di-vinyl monomers). More preferably, the diolefin monomers are linear di-vinyl monomers, most preferably those containing from 4 to 30 carbon atoms. Examples of preferred dienes include butadiene, pentadiene, hexadiene, heptadiene, octadiene, nonadiene, decadiene, undecadiene, dodecadiene, tridecadiene, tetradecadiene, pentadecadiene, hexadecadiene, heptadecadiene, octadecadiene, nonadecadiene, icosadiene, heneicosadiene, docosadiene, tricosadiene, tetracosadiene, pentacosadiene, hexacosadiene, heptacosadiene, octacosadiene, nonacosadiene, triacontadiene, particularly preferred dienes include 1,6-heptadiene, 1,7-octadiene, 1,8-nonadiene, 1,9-decadiene, 1,10-undecadiene, 1,11-dodecadiene, 1,12-tridecadiene, 1,13-tetradecadiene, and low molecular weight polybutadienes (Mw less than 1000 g/mol). Preferred cyclic dienes include cyclopentadiene, vinylnorbornene, norbornadiene, ethylidene norbornene, divinylbenzene, dicyclopentadiene or higher ring containing diolefins with or without substituents at various ring positions.

In a preferred embodiment one or more dienes are present in the polymer produced herein at up to 10 weight %, preferably at 0.00001 to 1.0 weight %, preferably 0.002 to 0.5 weight %, even more preferably 0.003 to 0.2 weight %, based upon the total weight of the composition. In some embodiments 500 ppm or less of diene is added to the polymerization, preferably 400 ppm or less, preferably or 300 ppm or less. In other embodiments at least 50 ppm of diene is added to the polymerization, or 100 ppm or more, or 150 ppm or more.

Preferred monomers include one or more of ethylene, propylene, butene-1, pentene-1,4-methyl-pentene-1, hexene-1, octene-1, decene-1,3-methyl-pentene-1, norbornene, norbornadiene, vinyl norbornene, ethylidene norbornene monomers.

In a particularly preferred embodiment the process of the invention relates to the polymerization of ethylene and at least one comonomer having from 4 to 8 carbon atoms, preferably 4 to 7 carbon atoms. Particularly, the comonomers are butene-1,4-methyl-pentene-1,3-methyl-pentene-1, hexene-1 and octene-1, the most preferred being hexene-1, butene-1 and octene-1.

In another preferred embodiment the polymer produced herein is a propylene homopolymer or copolymer. The comonomer is preferably a $C_4$ to $C_{20}$ linear, branched or cyclic monomer, and in one embodiment is a $C_4$ to $C_{12}$ linear or branched alpha-olefin, preferably butene, pentene, hexene, heptene, octene, nonene, decene, dodecene, 4-methylpentene-1,3-methyl pentene-1,3,5,5-trimethyl-hexene-1, and the like. Ethylene may be present at 5 mol % or less.

In another embodiment ethylene or propylene is polymerized with at least two different comonomers to form a terpolymer. The preferred comonomers are a combination of alpha-olefin monomers having 4 to 10 carbon atoms, more preferably 4 to 8 carbon atoms, optionally with at least one diene monomer. The preferred terpolymers include the combinations such as ethylene/butene-1/hexene-1, ethylene/propylene/butene-1, propylene/ethylene/hexene-1, ethylene/propylene/norbornene and the like.

In another embodiment, the olefin polymer comprises:
a first monomer present at from 40 to 95 mole %, preferably 50 to 90 mole %, preferably 60 to 80 mole %, and
a comonomer present at from 5 to 40 mole %, preferably 10 to 60 mole %, more preferably 20 to 40 mole %, and
a termonomer present at from 0 to 10 mole %, more preferably from 0.5 to 5 mole %, more preferably 1 to 3 mole %.

Typically, the first monomer comprises one or more of any $C_3$ to $C_8$ linear, branched or cyclic alpha-olefins, including propylene, butene (and all isomers thereof), pentene (and all isomers thereof), hexene (and all isomers thereof), heptene (and all isomers thereof), and octene (and all isomers thereof). Preferred monomers include propylene, 1-butene, 1-hexene, 1-octene, and the like.

The comonomer may comprise one or more of any $C_2$ to $C_{40}$ linear, branched or cyclic alpha-olefins (provided ethylene, if present, is present at 5 mole % or less), including ethylene, propylene, butene, pentene, hexene, heptene, and octene, nonene, decene, undecene, dodecene, hexadecene, styrene, 3,5,5-trimethylhexene-1,3-methylpentene-1,4-methylpentene-1, norbornene and cyclopentene.

The termonomer may comprise one or more of any $C_2$ to $C_{40}$ linear, branched or cyclic alpha-olefins, (provided ethylene, if present, is present at 5 mole % or less), including, but not limited to, ethylene, propylene, butene, pentene, hexene, heptene, and octene, nonene, decene, undecene, dodecene, hexadecene, butadiene, 1,5-hexadiene, 1,6-heptadiene, 1,4-pentadiene, 1,7-octadiene, 1,8-nonadiene, 1,9-decadiene, 1,11-dodecadiene, styrene, 3,5,5-trimethylhexene-1,3-methylpentene-1,4-methylpentene-1, and cyclopentadiene.

Polymerization Process

The catalyst systems described above are suitable for use in a solution, bulk, gas or slurry polymerization process or a combination thereof, preferably solution phase or bulk phase polymerization process.

In one embodiment, this invention is directed toward the solution, bulk, slurry or gas phase polymerization reactions involving the polymerization of one or more of monomers having from 3 to 30 carbon atoms, preferably 3-12 carbon atoms, and more preferably 3 to 8 carbon atoms. Preferred monomers include one or more of propylene, butene-1, pentene-1,4-methyl-pentene-1, hexene-1, octene-1, decene-1,3-methyl-pentene-1, and cyclic olefins or a combination thereof. Other monomers can include vinyl monomers, diolefins such as dienes, polyenes, norbornene, norbornadiene, vinyl norbornene, ethylidene norbornene monomers. Preferably a homopolymer or copolymer of propylene is produced. In another embodiment, both a homopolymer of propylene and a copolymer of propylene and one or more of the monomers listed above are produced.

One or more reactors in series or in parallel may be used in the present invention. Catalyst component and activator may be delivered as a solution or slurry, either separately to the reactor, activated in-line just prior to the reactor, or preactivated and pumped as an activated solution or slurry to the reactor. A preferred operation is two solutions activated in-line. For more information on methods to introduce multiple catalsyts into reactors, please see U.S. Pat. No. 6,399,722, and WO0130862A1. While these references may emphasize gas phase reactors, the techniques described are equally applicable to other types of reactors, including continuous stirred tank reactors, slurry loop reactors and the like. Polymerizations are carried out in either single reactor operation, in which monomer, comonomers, catalyst/activator, scavenger, and optional modifiers are added continuously to a single reactor or in series reactor operation, in which the above components are added to each of two or more reactors connected in series. The catalyst components can be added to the first reactor in the series. The catalyst component may also be added to both reactors, with one component being added to first reaction and another component to other reactors.

In one embodiment 500 ppm or less of hydrogen is added to the polymerization, or 400 ppm or less, or 300 ppm or less. In other embodiments at least 50 ppm of hydrogen is added to the polymerization, or 100 ppm or more, or 150 ppm or more.

Gas Phase Polymerization

Generally, in a fluidized gas bed process used for producing polymers, a gaseous stream containing one or more monomers is continuously cycled through a fluidized bed in the presence of a catalyst under reactive conditions. The gaseous stream is withdrawn from the fluidized bed and recycled back into the reactor. Simultaneously, polymer product is withdrawn from the reactor and fresh monomer is added to replace the polymerized monomer. (See for example U.S. Pat. Nos. 4,543,399, 4,588,790, 5,028,670, 5,317,036, 5,352,749, 5,405,922, 5,436,304, 5,453,471, 5,462,999, 5,616,661 and 5,668,228 all of which are fully incorporated herein by reference.)

Slurry Phase Polymerization

A slurry polymerization process generally operates between 1 to about 50 atmosphere pressure range (15 psi to 735 psi, 103 kPa to 5068 kPa) or even greater and temperatures in the range of 0° C. to about 120° C. In a slurry polymerization, a suspension of solid, particulate polymer is formed in a liquid polymerization diluent medium to which monomer and comonomers along with catalyst are added. The suspension including diluent is intermittently or continuously removed from the reactor where the volatile components are separated from the polymer and recycled, optionally after a distillation, to the reactor. The liquid diluent employed in the polymerization medium is typically an alkane having from 3 to 7 carbon atoms, preferably a branched alkane. The medium employed should be liquid under the conditions of polymerization and relatively inert. When a propane medium is used the process must be operated above the reaction diluent critical temperature and pressure. Preferably, a hexane or an isobutane medium is employed.

In one embodiment, a preferred polymerization technique useful in the invention is referred to as a particle form polymerization, or a slurry process where the temperature is kept below the temperature at which the polymer goes into solution. Such technique is well known in the art, and described in for instance U.S. Pat. No. 3,248,179 which is fully incorporated herein by reference. The preferred temperature in the particle form process is within the range of about 85° C. to about 110° C. Two preferred polymerization methods for the slurry process are those employing a loop reactor and those utilizing a plurality of stirred reactors in series, parallel, or combinations thereof. Non-limiting examples of slurry processes include continuous loop or stirred tank processes. Also, other examples of slurry processes are described in U.S. Pat. No. 4,613,484, which is herein fully incorporated by reference.

In another embodiment, the slurry process is carried out continuously in a loop reactor. The catalyst, as a slurry in isobutane or as a dry free flowing powder, is injected regularly to the reactor loop, which is itself filled with circulating slurry of growing polymer particles in a diluent of isobutane containing monomer and comonomer. Hydrogen, optionally, may be added as a molecular weight control. (In one embodiment 500 ppm or less of hydrogen is added, or 400 ppm or less or 300 ppm or less. In other embodiments at least 50 ppm of hydrogen is added, or 100 ppm or more, or 150 ppm or more).

The reactor is maintained at a pressure of 3620 kPa to 4309 kPa and at a temperature in the range of about 60° C. to about 104° C. depending on the desired polymer melting characterisitcs. Reaction heat is removed through the loop wall since much of the reactor is in the form of a double-jacketed pipe. The slurry is allowed to exit the reactor at regular intervals or continuously to a heated low pressure flash vessel, rotary dryer and a nitrogen purge column in sequence for removal of the isobutane diluent and all unreacted monomer and comonomers. The resulting hydrocarbon free powder is then compounded for use in various applications.

In one embodiment of the slurry process useful in the invention the concentration of predominant monomer in the reactor liquid medium is in the range of from about 1 to 10 weight percent, preferably from about 2 to about 7 weight percent, more preferably from about 2.5 to about 6 weight percent, most preferably from about 3 to about 6 weight percent.

Another process useful in the invention is where the process, preferably a slurry process is operated in the absence of or essentially free of any scavengers, such as triethylaluminum, trimethylaluminum, tri-isobutylaluminum and tri-n-hexylaluminum and diethyl aluminum chloride, dibutyl zinc and the like. This process is described in PCT publication WO 96/08520 and U.S. Pat. No. 5,712,352, which are herein fully incorporated by reference.

In another embodiment the process is run with scavengers. Typical scavengers include trimethyl aluminum, tri-isobutyl aluminum and an excess of alumoxane or modified alumoxane.

Homgeneous, Bulk or Solution Phase Polymerization

The catalysts described herein can be used advantageously in homogeneous solution processes. Generally this involves polymerization in a continuous reactor in which the polymer formed and the starting monomer and catalyst materials supplied, are agitated to reduce or avoid concentration gradients. Suitable processes operate above the melting point of the polymers at high pressures, from 1 to 3000 bar (10-30,000 MPa), in which the monomer acts as diluent or in solution polymerization using a solvent.

Temperature control in the reactor is obtained by balancing the heat of polymerization with reactor cooling by reactor jackets or cooling coils to cool the contents of the reactor, auto refrigeration, pre-chilled feeds, vaporization of liquid medium (diluent, monomers or solvent) or combinations of all three. Adiabatic reactors with pre-chilled feeds may also be used. The reactor temperature depends on the catalyst used. In general, the reactor temperature preferably can vary between about 30° C. and about 160° C., more preferably from about 90° C. to about 150° C., and most preferably from about 100° C. to about 140° C. Polymerization temperature may vary depending on catalyst choice. For example a diimine Ni catalyst may be used at 40° C., while a metallocene Ti catalyst can be used at 100° C. or more. In series operation, the second reactor temperature is preferably higher than the first reactor temperature. In parallel reactor operation, the temperatures of the two reactors are independent. The pressure can vary from about 1 mm Hg to 2500 bar (25,000 MPa), preferably from 0.1 bar to 1600 bar (1-16,000 MPa), most preferably from 1.0 to 500 bar (10-5000 MPa).

In one embodiment 500 ppm or less of hydrogen is added to the polymerization, or 400 ppm or less or 300 ppm or less. In other embodiments at least 50 ppm of hydrogen is added to the polymerization, or 100 ppm or more, or 150 ppm or more.

Each of these processes may also be employed in single reactor, parallel or series reactor configurations. The liquid processes comprise contacting olefin monomers with the above described catalyst system in a suitable diluent or solvent and allowing said monomers to react for a sufficient time to produce the desired polymers. Hydrocarbon solvents are suitable, both aliphatic and aromatic. Alkanes, such as hexane, pentane, isopentane, and octane, are preferred.

The process can be carried out in a continuous stirred tank reactor, batch reactor or plug flow reactor, or more than one reactor operated in series or parallel. These reactors may have or may not have internal cooling or heating and the monomer feed may or may not be refrigerated. See the disclosure of U.S. Pat. No. 5,001,205 for general process conditions. See also, international application WO 96/33227 and WO 97/22639. All documents are incorporated by reference for US purposes for description of polymerization processes, metallocene selection and useful scavenging compounds.

The invention will now be more particularly described with reference to the following non-limiting Examples.

EXAMPLES

In the Examples, pressure is reported in atmospheres and pounds per square inch. The conversion factors to S. I. Units are; 1 psi equals 6.894757 kPa and 1 atm equals 101.325 kPa.

Methods of Making the Metallocene Complexes

All manipulations of air- and/or water-sensitive compounds were performed under an argon atmosphere using standard Schlenk techniques. Prior to use, tetrahydrofuran (THF, Feida Industrial Trade Company), diethyl ether (Feida Industrial Trade Company), and petroleum ether (Feida Industrial Trade Company) were refluxed over sodium benzophenone ketyl and distilled under a dry argon atmosphere. Sodium wire and $HN(iPr)_2$ were purchased from Shanghai Linfeng Chemical and Reagent Company; $Me_2SiCl_2$, methylcyclopentadiene, and nBuLi, from Aldrich Chemical Company; cyclopentadiene, from Shanghai Petroleum Chemical Co., Ltd; and pyrrolidine and piperidine, from Shanghai Chemical and Reagent Company. The zirconium compounds $ZrCl_4(THF)_2$ (Manzer, L. E. *Inorg. Synth.* 1982, 21, 136) and $CpZrCl_3(DME)$ (Lund, E. C.; Livinghouse, T. *Organometallics* 1990, 9, 2426) were prepared according to published procedures. $^1H$ NMR spectra were recorded with a Bruker Avance-500 MHz. C, H, N microanalysis were obtained with an EA-1106 analyzer at Shanghai Institute of Organic Chemistry.

Outline of Reaction for Producing Compounds 1-9 and Complexes A-E

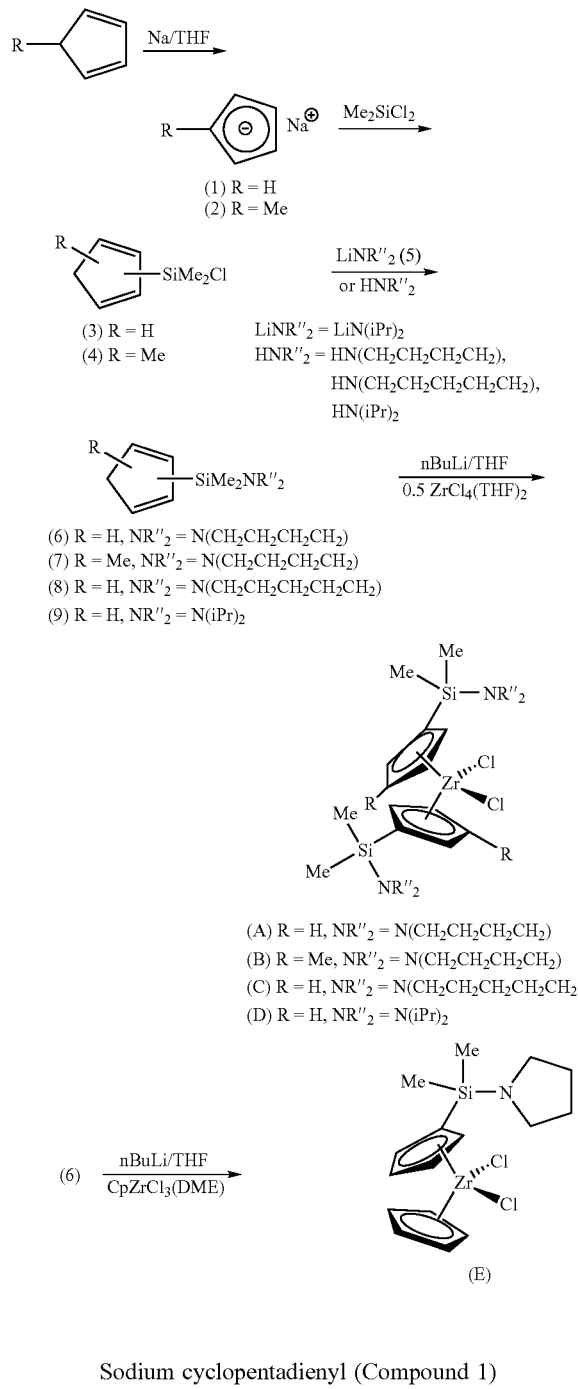

(1) R = H
(2) R = Me (3) R = H
(4) R = Me

LiNR″₂ = LiN(iPr)₂
HNR″₂ = HN(CH₂CH₂CH₂CH₂),
HN(CH₂CH₂CH₂CH₂CH₂),
HN(iPr)₂

(6) R = H, NR″₂ = N(CH₂CH₂CH₂CH₂)
(7) R = Me, NR″₂ = N(CH₂CH₂CH₂CH₂)
(8) R = H, NR″₂ = N(CH₂CH₂CH₂CH₂CH₂)
(9) R = H, NR″₂ = N(iPr)₂

(A) R = H, NR″₂ = N(CH₂CH₂CH₂CH₂)
(B) R = Me, NR″₂ = N(CH₂CH₂CH₂CH₂)
(C) R = H, NR″₂ = N(CH₂CH₂CH₂CH₂CH₂)
(D) R = H, NR″₂ = N(iPr)₂

Sodium cyclopentadienyl (Compound 1)

A suspension of sodium wire (9.2 g, 400 mmol) in 400 mL THF was cooled to 0° C., after which cyclopentadiene (26.4 g, 400 mmol) was added over a period of 1 hour. The reaction was stirred for an additional 2 hours, yielding a solution of NaCp.

Sodium methylcyclopentadienyl (Compound 2)

A suspension of sodium wire (11.3 g, 492 mmol) in 500 mL THF was cooled to 0° C., after which MeCp (40 mL, 470 mmol) was added over a period of 1 hour. The reaction was stirred for an additional 2 hours, yielding a solution of Na(MeCp).

(Chlorodimethylsilyl)cyclopentadiene (Compound 3)

A solution of Me₂SiCl₂ (225 mL, 1.86 mol) in 450 mL of diethyl ether was cooled to 0° C., after which a sodium cyclopentadiene (compound 1) solution (1.68 M, 950 mL, 1.60 mol) was added dropwise. A white precipitate formed immediately. The reaction was allowed to warm up to room temperature and was stirred for an additional 4 hours. The resulting reaction mixture was centrifuged to separate precipitate from supernatant. The volatiles of the isolated supernatant were removed in vacuo. Fractional distillation yielded 122.76 g (48%) of the desired product as a colorless liquid (48-52° C./15 mmHg).

(Chlorodimethylsilyl)methylcyclopentadiene (Compound 4)

A solution of Me₂SiCl₂ (270 mL, 2.23 mol) in 450 mL of diethyl ether was cooled to 0° C., after which 1050 mL of a 1.86 M solution of Na(MeCp) in THF was slowly added. A white precipitate formed immediately. The slurry was allowed to warm up to room temperature and was stirred for an additional 4 hours. The resulting reaction mixture was centrifuged to separate precipitate from supernatant. The volatiles of the isolated supernatant were removed in vacuo. Fractional distillation yielded 189.21 g (56%) of the desired product as a colorless liquid (57-59° C. at 9 mmHg).

Lithium diisopropylamine (Compound 5)

To a solution of HN(iPr)₂ (15.83 g, 156 mmol) in petroleum ether (50 mL), nBuLi (1.83 M, 80.2 mL, 147 mmol) was added over a period of 1 hour. The white precipitate was collected by filtration, yielding 13.8 g (88%) of LiN(iPr)₂.

(N-pyrrolidinyldimethylsilyl)cyclopentadiene (Compound 6)

A solution of CpSiMe₂Cl (compound 3, 16.49 g, 104 mmol) in 150 mL of diethyl ether was cooled to 0° C., after which pyrrolidine (17.37 mL, 208 mmol) was slowly added. A white precipitate formed immediately. The reaction was allowed to warm up to room temperature, stirred for an additional 4 hours, and filtered. The volatiles of the filtrate were removed in vacuo. Fractional distillation yielded 13.42 g (67%) of the desired colorless liquid (41-43° C./15 mmHg).

(N-pyrrolidinyldimethylsilyl)methylcyclopentadiene (Compound 7)

A solution of (MeCp)SiMe₂Cl (compound 4, 22.72 g, 132 mmol) in 200 mL of diethyl ether was cooled to 0° C., after which pyrrolidine (22.00 mL, 264 mmol) was slowly added. A white precipitate formed immediately. The reaction was allowed to warm up to room temperature, stirred for an additional 4 hours, and filtered. The volatiles of the filtrate were removed in vacuo. Fractional distillation yielded 17.46 g (64%) of the desired colorless liquid (52-54° C./1 mmHg).

(N-piperidinyldimethylsilyl)cyclopentadiene (Compound 8)

A solution of CpSiMe$_2$Cl (compound 3, 13.94 g, 88 mmol) in 200 mL of diethyl ether was cooled to 0° C., after which piperidine (17.40 mL, 176 mmol) was slowly added. A white precipitate formed immediately. The reaction was allowed to warm up to room temperature, stirred for an additional 4 hours, and filtered. The volatiles of the filtrate were removed in vacuo. Fractional distillation yielded 10.20 g (56%) of the desired colorless liquid (45-47° C./1 mmHg).

(N,N,-diisopropylaminodimethylsilyl)cyclopentadiene (Compound 9)

A solution of CpSiMe$_2$Cl (compound 3, 10.7 g, 67 mmol) in 50 mL of diethyl ether was cooled to −78° C., after which LiN(iPr)$_2$ (compound 5, 7.2 g, 67 mmol) in 150 mL of diethyl ether was added dropwise over a period of 1 hour. The reaction was stirred overnight and filtered. The volatiles of the filtrate were removed in vacuo. Fractional distillation yielded 6.8 g (45%) of the desired colorless product (53-55° C./0.03 mmHg).

Bis[N-pyrrolidinyldimethylsilyl)cyclopentadienyl] zirconium dichloride (Complex A)

A solution of compound 6 (3.40 g, 17.6 mmol) in 150 mL of THF was cooled to −70° C., after which nBuLi (1.85 M, 9.49 mL, 17.6 mmol) was added dropwise. The reaction was stirred at room temperature overnight, and then was added dropwise to a solution of ZrCl$_4$(THF)$_2$ (3.32 g, 8.80 mmol) in 50 mL of THF at −70° C. The reaction was stirred at room temperature overnight. Removal of volatiles in vacuo yielded a yellow solid residue. Crystallization of this residue from petroleum ether at low temperatures gave yellow crystals of the desired compound in 45% yield.

Anal. calc. for C$_{22}$H$_{36}$Cl$_2$N$_2$Si$_2$Zr: C, 48.31; H, 6.65; N, 5.12. Found: C, 48.19; H, 6.43; N, 4.90.

$^1$H NMR (CDCl$_3$): δ 6.67 (t, J=2.35 Hz, 4H, C$_5$H$_4$), 6.49 (t, J=2.35 Hz, 4H, C$_5$H$_4$), 3.22-2.85 (m, 8H, CH$_2$), 1.98-1.63 (m, 8H, CH$_2$), 0.4 (s, 12H, Si(CH$_3$)$_2$).

Bis[1-(N-pyrrolidinyldimethylsilyl)-3-methylcyclopentadienyl] zirconium dichloride (Complex B)

A solution of compound 7 (3.23 g, 15.6 mmol) in 80 mL of THF was cooled to −70° C., after which nBuLi (1.85 M, 8.47 mL, 15.67 mmol) was added dropwise. The reaction was stirred at room temperature overnight, and then was added dropwise to a solution of ZrCl$_4$(THF)$_2$ (2.94 g, 7.79 mmol) in 50 mL of THF at −70° C. The reaction was stirred at room temperature overnight. Removal of volatiles in vacuo yielded a yellow solid residue. Crystallization of this residue from petroleum ether at low temperatures gave yellow crystals of the desired compound in 36% yield.

Anal. calc. for C$_{24}$H$_{40}$Cl$_2$N$_2$Si$_2$Zr: C, 50.13; H, 7.03; N, 4.87. Found: C, 49.96; H, 6.87; N, 4.83.

$^1$H NMR (CDCl$_3$): δ 6.56 (t, J=2.37 Hz, 2H, C$_5$H$_3$), 6.50 (s, 2H, C$_5$H$_3$), 5.92 (d, J=2.01 Hz, 2H, C$_5$H$_3$), 3.30-2.85 (m, 8H, CH$_2$), 2.30 (s, 6H, CH$_3$ Cp), 2.00-1.65 (m, 8H, CH$_2$), 0.33 (s, 12H, Si(CH$_3$)$_2$).

Bis[(N-piperidinyldimethylsilyl)cyclopentadienyl] zirconium dichloride (Complex C)

A solution of compound 8 (2.81 g, 13.5 mmol) in 140 mL of THF was cooled to −70° C., after which nBuLi (1.85 M, 7.32 mL, 13.5 mmol) was added dropwise. The reaction was stirred at room temperature overnight, and then was added dropwise to a solution of ZrCl$_4$(THF)$_2$ (2.56 g, 6.79 mmol) in 50 mL of THF at −70° C. The reaction was stirred at room temperature overnight. Removal of volatiles in vacuo yielded a yellow solid residue. Crystallization of this residue from petroleum ether at low temperatures gave yellow crystals of the desired compound in 39% yield.

Anal. calc. for C$_{24}$H$_{40}$Cl$_2$N$_2$Si$_2$Zr: C, 50.13; H, 7.03; N, 4.87. Found: C, 49.79; H, 6.94; N, 5.06.

$^1$H NMR (CDCl$_3$): δ 6.67 (t, J=2.16 Hz, 4H, C$_5$H$_4$), 6.49 (t, J=2.16 Hz, 4H, C$_5$H$_4$), 2.78 (t, J=5.13 Hz, 8H, CH$_2$), 1.58-1.50 (m, 4H, CH$_2$), 1.39-1.31 (m, 8H, CH$_2$), 0.38 (s, 12H, Si(CH$_3$)$_2$).

Bis[(N,N-diisopropylaminodimethylsilyl)cyclopentadienyl] zirconium dichloride (Complex D)

A THF solution of Li(CpSiMe$_2$N(iPr)$_2$), prepared from compound 9 (1.83 g, 8.19 mmol) and nBuLi (1.83 M, 4.19 mL, 7.67 mmol), was added dropwise, over a period of 1 hour, to ZrCl$_4$(THF)$_2$ (1.54 g, 4.08 mmol) in 30 mL of THF at −78° C. The reaction was then stirred overnight at room temperature and the volatiles were removed in vacuo. Crystallization from petroleum ether yielded 1.08 g (46%) of white crystals.

Anal. calc. for C$_{26}$H$_{48}$Cl$_2$N$_2$Si$_2$Zr: C, 51.44; H, 7.99; N, 4.61. Found: C, 51.10; H, 7.78; N, 4.48.

$^1$H NMR (CDCl$_3$): δ 6.69 (m, 4H, C$_5$H$_4$), 6.45 (m, 4H, C$_5$H$_4$), 3.08 (m, J=6.77 Hz, 4H, CH(CH$_3$)$_2$), 0.98 (d, J=6.77 Hz, 24H, CH(CH$_3$)$_2$), 0.49 (s, 12H, Si(CH$_3$)$_2$).

[(N-pyrrolidinyldimethylsilyl)cyclopentadienyl][cyclopentadienyl] zirconium dichloride (Complex E)

A solution of compound 6 (1.25 g, 6.46 mmol) in 40 mL of THF was cooled to −70° C., after which nBuLi (1.84 M, 3.51 mL, 6.46 mmol) was added dropwise. The reaction was stirred at room temperature overnight, and then was added dropwise to a solution of CpZrCl$_3$(DME) (2.28 g, 6.46 mmol) in 50 mL of THF at −70° C. The reaction was stirred at room temperature overnight. Removal of volatiles in vacuo yielded a yellow solid residue. Crystallization of this residue from petroleum ether at low temperatures gave yellow crystals of the desired compound in 40% yield.

Anal. calc. for C$_{16}$H$_{23}$Cl$_2$NSiZr: C, 45.80; H, 5.54; N, 3.34. Found: C, 45.52; H, 5.83; N, 3.50.

$^1$H NMR (CDCl$_3$): δ 6.82-6.30 (m, 9H, C$_5$H$_4$ and C$_5$H$_5$), 3.33 (t, J=7.08 Hz, 4H, CH$_2$), 2.05-1.99 (m, 4H, CH$_2$), 0.23 (s, 6H, Si(CH$_3$)$_2$).

Polymerization Examples

All pre-catalysts were used as toluene solutions unless otherwise mentioned. Solutions were prepared in a dry box containing an inert atmosphere. Anhydrous toluene (99.8% packaged under nitrogen in Sure/Seal™ bottles) used for pre-catalyst solutions or slurries was purchased from Aldrich Chemical Company and stored in the dry box over 4A mole sieves. MAO (methylalumoxane, 10 wt % in toluene) was purchased from Albemarle Corporation. Catalyst solution concentration used was 1 mg of transition metal complex in 1 ml of toluene.

For experiments using ethylene, polymerization grade ethylene was used, it was further purified by passing it through two series of 500 cc columns, the first packed with molecular sieves (3A) activated at 600° C. and the second packed with Selexsorb CD (Coastal Chemicals). For experiments using propylene, the propylene was purified in the same manner as the ethylene. For experiments using 1-hexene, the 1-hexene (from Alfa Aesar) was sparged with nitrogen to remove air and stored over 4A mole sieves. The reactor solvent was high purity, dry and deoxygenated toluene (from ExxonMobil Chemical) stored under nitrogen gas and used as supplied. For additional information on drying solvents, see A. B. Pangborn, M. A. Giardello, R. H. Grubbs, R. K. Rosen, F. J. Timmers, *Organometallics* 1996, 15, 1518.

Polymerizations were conducted in a 0.5 L stainless steel Zipperclave reactor equipped with a paddle stirrer, a temperature controller, an on-demand supply of ethylene regulated to maintain a constant reactor pressure, and a supply of dry high pressure nitrogen to maintain an inert atmosphere. Monomer and solvent, directly plumbed into the reactor, were passed through drying columns prior to entering the reactor unless indicated otherwise.

Molecular weights (weight average molecular weight ($M_w$) and number average molecular weight ($M_n$)) were measured by Gel Permeation Chromatography using a Waters 150C Gel Permeation Chromatograph equipped with a differential refractive index detector and calibrated using polystyrene standards. BHT (2,6-di-tert-butyl-4-methylphenol) stabilized samples were run in 1,2,4-trichlorobenzene (145° C.) using three PLgel Mixed-B 10 µm (Polymer Laboratories) columns in series. No column spreading corrections were employed, but data on generally accepted standards, e.g. National Bureau of Standards Polyethylene 1475, demonstrated a precision with 0.1 units for $M_w/M_n$, which was calculated from elution times.

Polymer comonomer incorporation, branching and or end-group analysis was determined by $^1$H NMR using a Varian Unity+400 MHz instrument run with a single 30° flip angle, RF pulse. 120 pulses with a delay of 8 seconds between pulses were signal averaged. The polymer sample was dissolved in heated tetrachloroethane-$d^2$ and signal collection took place at 120° C. End-group analysis for examples reporting these numbers were measured by $^1$H NMR and were analyzed as follows. Vinylenes were measured as the number of vinylenes per 1000 carbon atoms using the resonances between 5.5-5.31 ppm. Trisubstituted end-groups ("trisubs") were measured as the number of trisubstituted groups per 1000 carbon atoms using the resonances between 5.3-4.85 ppm, by difference from vinyls. Vinyl end-groups were measured as the number of vinyls per 1000 carbon atoms using the resonances between 5.9-5.65 and between 5.3-4.85 ppm. Vinylidene end-groups were measured as the number of vinylidenes per 1000 carbon atoms using the resonances between 4.85-4.65 ppm.

Examples 1 to 6

A series of ethylene polymerizations was conducted by initially adding to the reactor vessel 200 mL of dry toluene and amount of 10 wt % methylalumoxane in toluene indicated in Table 1. Afterwards, the reactor was vented to reduce excess nitrogen pressure. The reactor was brought to 80° C., and the catalyst precursor dissolved in dry toluene and contained in a catalyst addition tube, was flushed into the reactor using the desired ethylene differential pressure. The reaction was run for 15 minutes during which time ethylene was added semi-continuously as needed to maintain reactor pressure. After the 15 minute time period, the ethylene flow was discontinued. The reactor was quickly cooled and vented. The reactor contents were precipitated in methanol. The polymer was initially dried under a flow of air and then typically dried overnight in a vacuum oven at 90 to 100° C. Polymerization results are tabulated in Table 1. Properties for the polymers of Examples 5 and 6 are listed in Table 2.

Examples 7 to 12

A series of ethylene/propylene copolymerization reactions was run by initially adding 100 mL of dry hexane and 10 wt % methylalumoxane in toluene to the reactor. The reactor was vented to reduce excess nitrogen pressure. Afterwards, 150 mL of propylene was added to the reactor and the reactor was heated to 80° C. The catalyst precursor, dissolved in dry toluene contained in a catalyst addition tube, was flushed into the reactor using the desired ethylene differential pressure. The reaction was run for 15 minutes at which time the reactor was quickly cooled and vented. The reactor contents were precipitated in methanol. The polymer was initially dried under a flow of air and then typically dried overnight in a vacuum oven at 90 to 100° C. Polymerization results are tabulated in Table 1.

Examples 13 to 18

A series of ethylene/1-hexene copolymerization reactions was begun by adding 175 mL of dry toluene and 10 wt % methylalumoxane in toluene to the reactor. The reactor was vented to reduce excess nitrogen pressure. Afterwards, 25 mL of 1-hexene was cannulated into the reactor, and the reactor was heated to 80° C. The catalyst precursor, dissolved in dry toluene contained in a catalyst addition tube, was flushed into the reactor using the desired ethylene differential pressure. The reaction was run for 15 minutes at which time the reactor was quickly cooled and vented. The reactor contents were precipitated in methanol. The polymer was initially dried under a flow of air and then typically dried overnight in a vacuum oven at 90 to 100° C. Polymerization results are tabulated in Table 1.

Examples 19 to 24

A series of propylene polymerization reactions was begun by adding 125 mL of dry toluene and 10 wt % methylalumoxane in toluene to the reactor. The reactor was vented to reduce excess nitrogen pressure. Afterwards, 125 mL of propylene was added to the reactor and the reactor was heated to 60° C. The catalyst precursor, dissolved in dry toluene contained in a catalyst addition tube, was flushed into the reactor using approximately 5-10 mL of dry toluene under nitrogen pressure. The reaction was run for 30 minutes at which time the reactor was quickly cooled and vented. The reactor contents were precipitated in methanol. The polymer was initially dried under a flow of air and then typically dried overnight in a vacuum oven at 90 to 100° C. Polymerization results are tabulated in Table 1.

In Table 1, TMC refers to the identity of the transition metal compound (pre-catalyst=catalyst precursor) used. Al/M is the molar aluminum to transition metal ratio used.

$C_2H_2$ is the differential pressure of ethylene in atmospheres that was semi-continuously fed to the reactor. Polymer (g) is the weight of polymer produced. In some cases, residual ash was also present and contributed to this weight. Activity is the catalyst activity measured as kg of polymer per mole of transition metal compound per atmosphere of ethylene per hour (kg P/mol TMC·atm·hr) for reactions using ethylene, and as kg of polymer per mole of transition metal compound per hour (kg P/mol TMC·hr) for reactions not using ethylene.

In Table 2, Mw is weight average molecular weight of the polymer and Mn is the number average molecular weight of the polymer, both as measured by GPC. Branching is the amount of short chain branching and long chain branching in the polymer as measured by $^1$H NMR. It is reported as the number of branches per 1000 carbon atoms and not corrected for chain end-groups. Vinylenes, trisubs, vinyls, and vinylidenes are respectively, the number of vinylene end-groups, trisubstituted end-groups, vinyl end-groups and vinylidene end-groups measured as the number of the respective end-groups per 1000 carbon atoms via $^1$H NMR.

TABLE 1

| Ex # | Type of Run | TMC | TMC (µmol) | MAO (ml) | Al/M (molar) | C2 (atm) | P (g) | Activity |
|---|---|---|---|---|---|---|---|---|
| 1 | PE | D | 0.988 | 1.20 | 1214 | 4.49 | 2.4 | 2,190 |
| 2 | PE | D | 0.988 | 1.20 | 1214 | 4.49 | 1.9 | 1,712 |
| 3 | PE | A | 1.829 | 2.30 | 1258 | 4.49 | 6.0 | 2,918 |
| 4 | PE | A | 1.829 | 2.30 | 1258 | 4.49 | 4.7 | 2,290 |
| 5 | PE | E | 0.953 | 1.20 | 1259 | 4.42 | 7.6 | 7,183 |
| 6 | PE | E | 0.953 | 1.20 | 1259 | 4.42 | 9.1 | 8,607 |
| 7 | EP | D | 3.954 | 2.00 | 506 | 4.79 | 36.7 | 7,742 |
| 8 | EP | D | 3.954 | 2.00 | 506 | 4.79 | 41.5 | 8,759 |
| 9 | EP | A | 5.486 | 2.80 | 510 | 4.76 | 15.0 | 2,297 |
| 10 | EP | A | 5.486 | 2.80 | 510 | 4.85 | 17.9 | 2,685 |
| 11 | EP | E | 4.767 | 2.40 | 503 | 4.76 | 34.7 | 6,117 |
| 12 | EP | E | 4.767 | 2.40 | 503 | 4.76 | 34.3 | 6,046 |
| 13 | EH | D | 3.954 | 2.00 | 506 | 4.49 | 6.7 | 1,512 |
| 14 | EH | D | 3.954 | 2.00 | 506 | 4.49 | 6.1 | 1,374 |
| 15 | EH | A | 5.486 | 2.80 | 510 | 4.49 | 7.1 | 1,155 |
| 16 | EH | A | 5.486 | 2.80 | 510 | 4.42 | 8.2 | 1,350 |
| 17 | EH | E | 4.767 | 2.40 | 503 | 4.56 | 22.8 | 4,198 |
| 18 | EH | E | 4.767 | 2.40 | 503 | 4.56 | 21.9 | 4,023 |
| 19 | PP | D | 3.954 | 2.0 | 506 | 0 | 14.2 | 7,167 |
| 20 | PP | D | 3.954 | 2.0 | 506 | 0 | 12.0 | 6,090 |
| 21 | PP | A | 7.315 | 3.7 | 506 | 0 | 5.7 | 1,550 |
| 22 | PP | A | 7.315 | 3.7 | 506 | 0 | 6.9 | 1,887 |
| 23 | PP | E | 4.767 | 2.4 | 503 | 0 | 14.4 | 6,059 |
| 24 | PP | E | 4.767 | 2.4 | 503 | 0 | 14.0 | 7,364 |

TABLE 1

| Ex # | Mw | Mn | MWD | Vinylenes/ 1000 C. | Trisubstituted/ 1000 C. | Vinyls/ 1000 C. | Vinylidenes/ 1000 C. |
|---|---|---|---|---|---|---|---|
| 5 | 85,223 | 34,780 | 2.45 | 0.14 | 0.07 | 0.20 | 0.02 |
| 6 | 98,534 | 35,631 | 2.77 | 0.16 | 0.06 | 0.20 | 0.05 |

All documents described herein are incorporated by reference herein, including any priority documents and/or testing procedures. As is apparent from the foregoing general description and the specific embodiments, while forms of the invention have been illustrated and described, various modifications can be made without departing from the spirit and scope of the invention. Accordingly, it is not intended that the invention be limited thereby.

The invention claimed is:

1. A metallocene complex represented by the formula $(C_pR_5)_nMX_k$ where each occurrence of $C_p$ is a cyclopentadienyl group;
each of the five R substituents on the cyclopentadienyl group is independently selected from the group consisting of hydrogen, $C_1$ to $C_{30}$ substituted or unsubstituted hydrocarbyl, halohydrocarbyl, silylhydrocarbyl, silylhalohydrocarbyl, and $SiR'_2NR''_2$ where each of the two R' substituents is independently selected from the group consisting of $C_1$ to $C_{30}$ substituted or unsubstituted hydrocarbyl, halohydrocarbyl, silylhydrocarbyl, and silylhalohydrocarbyl, wherein two adjacent R' substituents may be joined to form part of a saturated, partially unsaturated or aromatic monocyclic or polycyclic ring structure, and each of the two R'' substituents is independently selected from the group consisting of $C_3$ to $C_{30}$ substituted or unsubstituted hydrocarbyl, halohydrocarbyl, silylhydrocarbyl and silylhalohydrocarbyl, wherein two adjacent R'' substituents may be joined to form part of a saturated, partially unsaturated or aromatic monocyclic or polycyclic ring structure, and where a R' and a R'' may join together to form part of a monocyclic or polycyclic ring structure, and wherein two adjacent R substituents on a cyclopentadienyl group may be joined to form part of a saturated, partially unsaturated or aromatic monocyclic or polycyclic ring structure;
n is 1 or 2;
M is a metal of valence m from Group 4 of the Periodic Table of Elements,
k is equal to m minus n and is 2 or 3 where m is the valence of M; and
each X substituent is a univalent anionic ligand, or two X substituents are joined and bound to the metal atom to form a metallocycle ring, or two X substituents are joined to form a chelating ligand, a diene ligand, or an alkylidene ligand,
provided that: (1) at least one R substituent on the cyclopentadienyl group is $SiR'_2NR''_2$; and (2) the $C_p$ may be bridged by a bridging group to another $C_p$ group where the bridging group replaces one R group on the $C_p$ group(s) or the $C_p$ may be bridged by a bridging group to a heteroatom containing group where the bridging group replaces a hydrogen on the heteratom containing group; and (3) when n is 2, M is Hf or Zr.

2. The complex of claim 1 and including a single $SiR'_2NR''_2$ substituent.

3. The complex of claim 2, wherein the remaining R substituents are independently selected from the group consisting of hydrogen and methyl.

4. The complex of claim 2, wherein n is 1.

5. The complex of claim 1, wherein n is 2 and one R substituent on each cyclopentadienyl group is $SiR'_2NR''_2$.

6. The complex of claim 5, wherein the remaining R substituents on each cyclopentadienyl group are hydrogen.

7. A metallocene complex represented by the formula $$(C_pR_5)_nMX_k$$

where each occurrence of $C_p$ is a cyclopentadienyl group; each of the five R substituents on the cyclopentadienyl group is independently selected from the group consisting of hydrogen, $C_1$ to $C_{30}$ substituted or unsubstituted hydrocarbyl, halohydrocarbyl, silylhydrocarbyl or silylhalohydrocarbyl, and $SiR'_2NR''_2$ where each of the two R' substituents is independently selected from $C_1$ to $C_{30}$ substituted or unsubstituted hydrocarbyl, halohydrocarbyl, silylhydrocarbyl and silylhalohydrocarbyl, wherein two adjacent R' substituents may be joined to form part of a saturated, partially unsaturated or aromatic monocyclic or polycyclic ring structure, and each of the two R'' substituents is independently selected from the group consisting of $C_3$ to $C_{30}$ substituted or unsubstituted hydrocarbyl, halohydrocarbyl, silylhydrocarbyl, and silylhalohydrocarbyl, wherein two adjacent R'' substituents may be joined to form part of a saturated, partially unsaturated or aromatic monocyclic or polycyclic ring structure, and where a R' and a R'' may joined together to form part of a monocyclic or polycyclic ring structure, and wherein two adjacent R substituents on a cyclopentadienyl group may be joined to from part of a saturated, partially unsaturated or aromatic monocyclic or polycyclic ring structure;

n is 2;

M is Ti, Hf or Zr, k is 2 and m is 4; and each X substituent is a univalent anionic ligand, or two X substituents are joined and bound to the metal atom to form a metallocycle ring, or two X substituents are joined to form a chelating ligand, a diene ligand, or an alkylidene ligand, provided that at least one R substituent on the cyclopentadienyl group is $SiR'_2NR''_2$ and wherein the cyclopentadienyl groups are bridged by a bridging group including at least one R substituent from each cyclopentadienyl group.

8. The complex of claim 7, wherein the bridging group comprises $R_2C$, $R_2Si$, $R_2Ge$, $R_2CCR_2$, $R_2CCR_2CR_2$, $R_2CCR_2CR_2CR_2$, $RC$=$CR$, $RC$=$CRCR_2$, $R_2CCR$=$CRCR_2$, $RC$=$CRCR$=$CR$, $RC$=$CRCR_2CR_2$, $R_2CSiR_2$, $R_2SiSiR_2$, $R_2CSiR_2CR_2$, $R_2SiCR_2SiR_2$, $RC$=$CRSiR_2$, $R_2CGeR_2$, $R_2GeGeR_2$, $R_2CGeR_2CR_2$, $R_2GeCR_2GeR_2$, $R_2SiGeR_2$, $RC$=$CRGeR_2$, $RB$, $R_2C$—$BR$, $R_2C$—$BR$—$CR_2$, $RN$, $RP$, $O$, $S$, $Se$, $R_2C$—$O$—$CR_2$, $R_2CR_2C$—$O$—$CR_2CR_2$, $R_2C$—$O$—$CR_2CR_2$, $R_2C$—$O$—$CR$=$CR$, $R_2C$—$S$—$CR_2$, $R_2CR_2C$—$S$—$CR_2CR_2$, $R_2C$—$S$—$CR_2CR_2$, $R_2C$—$S$—$CR$=$CR$, $R_2C$—$Se$—$CR_2$, $R_2CR_2C$—$Se$—$CR_2CR_2$, $R_2C$—$Se$—$CR_2CR_2$, $R_2C$—$Se$—$CR$=$CR$, $R_2C$—$N$=$CR$, $R_2C$—$NR$—$CR_2$, $R_2C$—$NR$—$CR_2CR_2$, $R_2C$—$NR$—$CR$=$CR$, $R_2CR_2C$—$NR$—$CR_2CR_2$, $R_2C$—$P$=$CR$ or $R_2C$—$PR$—$CR_2$.

9. The complex of claim 1, wherein each R' substituent is $C_1$ to $C_{12}$ hydrocarbyl.

10. The complex of claim 1, wherein each R' substituent is methyl.

11. A metallocene complex represented by the formula $$(C_pR_5)_nMX_k$$

where each occurrence of $C_p$ is a cyclopentadienyl group; each of the five R substituents on the cyclopentadienyl group is independently selected from the group consisting of hydrogen, $C_1$ to $C_{30}$ substituted or unsubstituted hydrocarbyl, halohydrocarbyl, silylhydrocarbyl, silylhalohydrocarbyl, and $SiR'_2NR''_2$ where each of the two R' substituents is independently selected from the group consisting of $C_1$ to $C_{30}$ substituted or unsubstituted hydrocarbyl, halohydrocarbyl, silylhydrocarbyl and silylhalohydrocarbyl, wherein two adjacent R' substituents may be joined to form part of a saturated, partially unsaturated or aromatic monocyclic or polycyclic ring structure, and two adjacent R'' substituents may be joined to form part of a saturated, partially unsaturated or aromatic monocyclic or polycyclic ring structure, and where a R' and a R'' may join together to form part of a monocyclic or polycyclic ring structure, and wherein two adjacent R substituents on a cyclopentadienyl group may be joined to form part of a saturated, partially unsaturated or aromatic monocyclic or polycyclic ring structure;

n is 2;

M is Hf or Zr, k is equal to m minus n and is 1 or 2, where m is the valence of M; and each X substituent is a univalent anionic ligand, or two X substituents are joined and bound to the metal atom to form a metallocycle ring, or two X substituents are joined to form a chelating ligand, a diene ligand, or an alkylidene ligand, provided that the $C_p$ may be bridged by a bridging group to another $C_p$ group where the bridging group replaces one R group on the $C_p$ group(s) or the $C_p$ may be bridged by a bridging group to a heteroatom containing group where the bridging group replaces a hydrogen on the heteratom containing group, and provided that at least one R substituent on the each cyclopentadienyl group is $SiR'_2NR''_2$ and provided that each R'' substituent is a $C_3$ to $C_{12}$ hydrocarbyl.

12. The complex of claim 11, wherein each R'' substituent is iso-propyl.

13. The complex of claim 1, wherein the R'' substituents of each $SiR'_2NR''_2$ group are joined such that the $NR''_2$ moiety forms a five or six membered nitrogen-containing ring.

14. The complex of claim 13, wherein said five or six membered nitrogen-containing ring comprises a pyrrolidinyl or piperidinyl ring.

15. The complex of claim 1 wherein the R' substituents of one or each $SiR'_2NR''_2$ group are joined such that the $SiR'_2$ moiety forms a five or six membered silicon-containing ring.

16. The complex of claim 1 wherein one R' substituent of the $SiR'_2NR''_2$ group is joined to an R'' substituent of the same $SiR'_2NR''_2$ group such that the R'—Si—NR'' moiety forms a five or six membered ring.

17. The complex of claim 1, wherein M is zirconium.

18. A metallocene complex represented by the formula I, II, III, or IV:

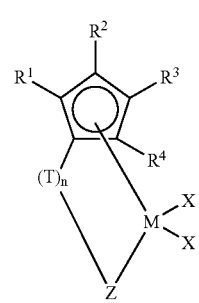

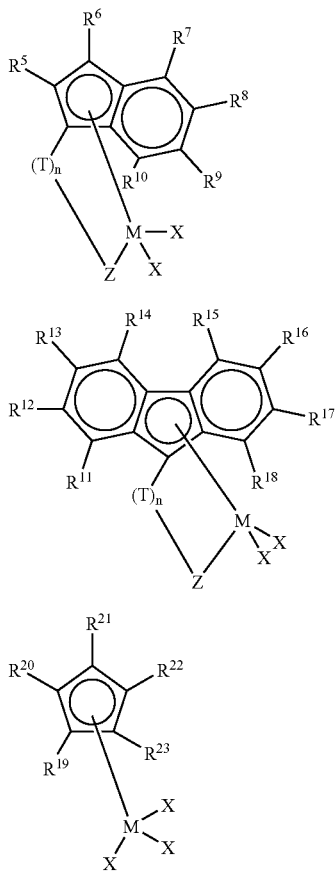

where M is Ti, Hf or Zr;

T is a bridging group;

n is 0 or 1;

X is a univalent anionic ligand;

Z is a substituted or unsubstituted cyclopentadienyl group, a substituted or unsubstituted indenyl group, a substituted or unsubstituted fluorenyl group, or a heteroatom containing group;

$R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, and $R^{23}$ are independently selected from the group consisting of hydrogen, substituted or unsubstituted hydrocarbyl, halohydrocarbyl, silylhydrocarbyl and silylhalohydrocarbyl groups, wherein two adjacent R substituents may form all or part of a saturated, partially unsaturated or aromatic monocyclic or polycyclic ring structure, provided that at least one of $R^1$, $R^2$, $R^3$, or $R^4$ in formula I, at least one of $R^5$, $R^6$, $R^7$, $R^8$, $R^9$, or $R^{10}$ in formula II, at least one of $R^{11}$, $R^{12}$, $R^{13}$, $R^{14}$, $R^{15}$, $R^{16}$, $R^{17}$, or $R^{18}$ in formula III, or at least one of $R^{19}$, $R^{20}$, $R^{21}$, $R^{22}$, or $R^{23}$ in formula IV is an Si—N group represented by the formula:

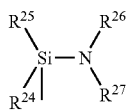

where $R^{24}$, $R^{25}$, $R^{26}$ and $R^{27}$ are, independently, substituted or unsubstituted hydrocarbyl groups, where at least one of $R^{26}$ and $R^{27}$ has at least 3 carbon atoms, and, optionally, where two adjacent $R^{24}$, $R^{25}$, $R^{26}$ and $R^{27}$ substituents may be joined to form part of a monocyclic or polycyclic ring structure.

19. The metallocene complex of claim 18 wherein the complex is represented by the formula I, II or III and where:
   a) n is 1 and T is a silyl group substituted with two $C_1$ to $C_{12}$ hydrocarbyl groups;
   b) each X is independently a $C_1$ to $C_{20}$ hydrocarbyl group or a halogen;
   c) Z is substituted with two, three or four of said Si—N groups;
   d) two, three or four of $R^1$, $R^2$, $R^3$, or $R^4$ are said Si—N groups, or two, three or four of $R^5$, $R^6$, $R^7$, $R^8$, $R^9$, or $R^{10}$ are said Si—N groups, or two, three or four of $R^{11}$, $R^{12}$, $R^{13}$, $R^{14}$, $R^{15}$, $R^{16}$, $R^{17}$, or $R^{18}$ are said Si—N groups;
   e) $R^{24}$ and $R^{25}$ are independently a $C_1$ to $C_{12}$ hydrocarbyl group; and
   f) $R^{26}$ and $R^{27}$ are, independently, a $C_3$ to $C_{12}$ hydrocarbyl group or form a substituted or unsubstituted pyrrolidinyl or piperidinyl ring.

20. The metallocene complex of claim 18 wherein the complex is represented by the formula IV and where:
   a) each X is independently a $C_1$ to $C_{20}$ hydrocarbyl group or a halogen;
   b) two, three or four of $R^{19}$, $R^{20}$, $R^{21}$, $R^{22}$, or $R^{23}$ are said Si—N groups;
   c) $R^{24}$ and $R^{25}$ are independently a $C_1$ to $C_{12}$ hydrocarbyl group; and
   d) $R^{26}$ and $R^{27}$ are, independently, a $C_2$ to $C_{12}$ hydrocarbyl group or form a substituted or unsubstituted pyrrolidinyl or piperidinyl ring.

21. The metallocene complex of claim 18 wherein $R^{25}$ and $R^{26}$ are joined to form a cyclic structure represented by the following formula:

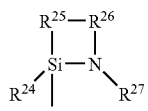

where $R^{24}$ is as defined above, except that $R^{24}$ and $R^{25}$ do not form a cyclic structure;

$R^{27}$ is as defined above, except that $R^{27}$ and $R^{26}$ do not form a cyclic structure;

$R^{25}$ is a $C_1$ to $C_{20}$ hydrocarbyl group or a $C_1$ to $C_{20}$ substituted hydrocarbyl group, and $R^{26}$ is a $C_{12}$ to $C_{20}$ hydrocarbyl group or a $C_1$ to $C_{20}$ substituted hydrocarbyl group.

22. The metallocene complex of claim 1 comprising at least one of:
   Bis[(N-pyrrolidinyldimethylsilyl)cyclopentadienyl] zirconium dichloride,
   Bis[1-(N-pyrrolidinyldimethylsilyl)-3-methylcyclopentadienyl] zirconium dichloride,
   Bis[(N-piperidinyldimethylsilyl)cyclopentadienyl] zirconium dichloride,
   Bis[(N,N-diisopropylaminodimethylsilyl)cyclopentadienyl] zirconium dichloride,
   [(N-pyrrolidinyldimethylsilyl)cyclopentadienyl] [cyclopentadienyl] zirconium dichloride, Bis[(N-pyrrolidinyldimethylsilyl)cyclopentadienyl] zirconium dibromide,
Bis[1-(N-pyrrolidinyldimethylsilyl)-3-methylcyclopentadienyl] zirconium dibromide,
Bis[(N-piperidinyldimethylsilyl)cyclopentadienyl] zirconium dibromide,
Bis[(N,N-diisopropylaminodimethylsilyl)cyclopentadienyl] zirconium dibromide,
[(N-pyrrolidinyldimethylsilyl)cyclopentadienyl] [cyclopentadienyl] zirconium dibromide,
Bis[(N-pyrrolidinyldimethylsilyl)cyclopentadienyl] zirconium difluoride,
Bis[1-(N-pyrrolidinyldimethylsilyl)-3-methylcyclopentadienyl] zirconium difluoride,
Bis[(N-piperidinyldimethylsilyl)cyclopentadienyl] zirconium difluoride,
Bis[(N,N-diisopropylaminodimethylsilyl)cyclopentadienyl] zirconium difluoride,
[(N-pyrrolidinyldimethylsilyl)cyclopentadienyl] [cyclopentadienyl] zirconium difluoride,
Bis[(N-pyrrolidinyldimethylsilyl)cyclopentadienyl] zirconium dimethyl,
Bis[1-(N-pyrrolidinyldimethylsilyl)-3-methylcyclopentadienyl] zirconium dimethyl,
Bis[(N-piperidinyldimethylsilyl)cyclopentadienyl] zirconium dimethyl,
Bis[(N,N-diisopropylaminodimethylsilyl)cyclopentadienyl] zirconium dimethyl,
[(N-pyrrolidinyldimethylsilyl)cyclopentadienyl] [cyclopentadienyl] zirconium dimethyl,
Bis[(N-pyrrolidinyldimethylsilyl)cyclopentadienyl] zirconium diethyl,
Bis[1-(N-pyrrolidinyldimethylsilyl)-3-methylcyclopentadienyl] zirconium diethyl,
Bis[(N-piperidinyldimethylsilyl)cyclopentadienyl] zirconium diethyl,
Bis[(N,N-diisopropylaminodimethylsilyl)cyclopentadienyl] zirconium diethyl,
[(N-pyrrolidinyldimethylsilyl)cyclopentadienyl] [cyclopentadienyl] zirconium diethyl,
Bis[(N-pyrrolidinyldimethylsilyl)cyclopentadienyl] zirconium dimethoxide,
Bis[1-(N-pyrrolidinyldimethylsilyl)-3-methylcyclopentadienyl] zirconium dimethoxide,
Bis[(N-piperidinyldimethylsilyl)cyclopentadienyl] zirconium dimethoxide,
Bis[(N,N-diisopropylaminodimethylsilyl)cyclopentadienyl] zirconium dimethoxide,
[(N-pyrrolidinyldimethylsilyl)cyclopentadienyl] [cyclopentadienyl] zirconium dimethoxide,
Bis[(N-pyrrolidinyldimethylsilyl)cyclopentadienyl] zirconium diethoxide,
Bis[1-(N-pyrrolidinyldimethylsilyl)-3-methylcyclopentadienyl] zirconium diethoxide,
Bis[(N-piperidinyldimethylsilyl)cyclopentadienyl] zirconium diethoxide,
Bis[(N,N-diisopropylaminodimethylsilyl)cyclopentadienyl] zirconium diethoxide,
[(N-pyrrolidinyldimethylsilyl)cyclopentadienyl] [cyclopentadienyl] zirconium diethoxide,
Bis[(N-pyrrolidinyldimethylsilyl)cyclopentadienyl] hafnium dichloride,
Bis[1-(N-pyrrolidinyldimethylsilyl)-3-methylcyclopentadienyl] hafnium dichloride,
Bis[(N-piperidinyldimethylsilyl)cyclopentadienyl] hafnium dichloride,
Bis[(N,N-diisopropylaminodimethylsilyl)cyclopentadienyl] hafnium dichloride,
[(N-pyrrolidinyldimethylsilyl)cyclopentadienyl] [cyclopentadienyl] hafnium dichloride,
Bis[(N-pyrrolidinyldimethylsilyl)cyclopentadienyl] hafnium dibromide,
Bis[1-(N-pyrrolidinyldimethylsilyl)-3-methylcyclopentadienyl] hafnium dibromide,
Bis[(N-piperidinyldimethylsilyl)cyclopentadienyl] hafnium dibromide,
Bis[(N,N-diisopropylaminodimethylsilyl)cyclopentadienyl] hafnium dibromide,
[(N-pyrrolidinyldimethylsilyl)cyclopentadienyl] [cyclopentadienyl] hafnium dibromide,
Bis[(N-pyrrolidinyldimethylsilyl)cyclopentadienyl] hafnium difluoride,
Bis[1-(N-pyrrolidinyldimethylsilyl)-3-methylcyclopentadienyl] hafnium difluoride,
Bis[(N-piperidinyldimethylsilyl)cyclopentadienyl] hafnium difluoride,
Bis[(N,N-diisopropylaminodimethylsilyl)cyclopentadienyl] hafnium difluoride,
[(N-pyrrolidinyldimethylsilyl)cyclopentadienyl] [cyclopentadienyl] hafnium difluoride,
Bis[(N-pyrrolidinyldimethylsilyl)cyclopentadienyl] hafnium dimethyl,
Bis[1-(N-pyrrolidinyldimethylsilyl)-3-methylcyclopentadienyl] hafnium dimethyl,
Bis[(N-piperidinyldimethylsilyl)cyclopentadienyl] hafnium dimethyl,
Bis[(N,N-diisopropylaminodimethylsilyl)cyclopentadienyl] hafnium dimethyl,
[(N-pyrrolidinyldimethylsilyl)cyclopentadienyl] [cyclopentadienyl] hafnium dimethyl,
Bis[(N-pyrrolidinyldimethylsilyl)cyclopentadienyl] hafnium diethyl,
Bis[1-(N-pyrrolidinyldimethylsilyl)-3-methylcyclopentadienyl] hafnium diethyl,
Bis[(N-piperidinyldimethylsilyl)cyclopentadienyl] hafnium diethyl,
Bis[(N,N-diisopropylaminodimethylsilyl)cyclopentadienyl] hafnium diethyl,
[(N-pyrrolidinyldimethylsilyl)cyclopentadienyl] [cyclopentadienyl] hafnium diethyl,
Bis[(N-pyrrolidinyldimethylsilyl)cyclopentadienyl] hafnium dimethoxide,
Bis[1-(N-pyrrolidinyldimethylsilyl)-3-methylcyclopentadienyl] hafnium dimethoxide,
Bis[(N-piperidinyldimethylsilyl)cyclopentadienyl] hafnium dimethoxide,
Bis[(N,N-diisopropylaminodimethylsilyl)cyclopentadienyl] hafnium dimethoxide,
[(N-pyrrolidinyldimethylsilyl)cyclopentadienyl] [cyclopentadienyl] hafnium dimethoxide,
Bis[(N-pyrrolidinyldimethylsilyl)cyclopentadienyl] hafnium diethoxide,
Bis[1-(N-pyrrolidinyldimethylsilyl)-3-methylcyclopentadienyl] hafnium diethoxide,
Bis[(N-piperidinyldimethylsilyl)cyclopentadienyl] hafnium diethoxide,
Bis[(N,N-diisopropylaminodimethylsilyl)cyclopentadienyl] hafnium diethoxide, and
[(N-pyrrolidinyldimethylsilyl)cyclopentadienyl] [cyclopentadienyl] hafnium diethoxide.

* * * * *